United States Patent [19]
Silvern

[11] Patent Number: 6,095,975
[45] Date of Patent: Aug. 1, 2000

[54] APPARATUS AND METHOD FOR DETERMINING OPTIMAL LOCATIONS TO PLACE RADIOACTIVE SEEDS AT A CANCEROUS SITE

[76] Inventor: David A. Silvern, 12 Sulgrave Rd., Scarsdale, N.Y. 10583

[21] Appl. No.: 08/864,068

[22] Filed: May 27, 1997

[51] Int. Cl.[7] ........................................................ A61B 8/00
[52] U.S. Cl. .............................. 600/439; 128/922; 600/3
[58] Field of Search ................................. 600/439, 3–9; 128/920–924

[56] References Cited

U.S. PATENT DOCUMENTS

| | | | |
|---|---|---|---|
| 5,647,663 | 7/1997 | Holmes | 128/922 |
| 5,666,954 | 9/1997 | Chapelon et al. | 600/439 |
| 5,759,162 | 6/1998 | Oppelt et al. | 600/439 |
| 5,820,559 | 10/1998 | Ng et al. | 600/439 |

OTHER PUBLICATIONS

A Genetic Algorithm for the Optimization of Prostate Implants, Yan Yu and M.C. Schell Medical Physics, vol. 23, No. 12, Dec. 1996, pp. 2085–2091.

*Primary Examiner*—Francis J. Jaworski
*Attorney, Agent, or Firm*—McAulay Nissen Goldberg Kiel & Hand, LLP

[57] ABSTRACT

An apparatus and method for determining optimal locations for placing radioactive seeds at a cancerous site. After a plurality of cross-sectional images of the cancerous site are obtained, a contour of an area on each cross-sectional image of the cancerous site is defined and transferred to a three-dimensional coordinate system. Then, a population of locations within each area of each cross-sectional image of the cancerous site where radioactive seeds can be placed is identified. A genetic algorithm is then implemented to determine the optimal number of locations within the cancerous site to place the radioactive seeds.

12 Claims, 28 Drawing Sheets

35   35

|   | L=0 | L=1 | L=2 | L=3 | L=4 | L=5 | L=6 |
|---|-----|-----|-----|-----|-----|-----|-----|
| E | 0 | 0 | 1 | 1 | 0 | 0 | 0 |
| F | 0 | 1 | 0 | 0 | 0 | 1 | 1 |
| H | 0 | 1 | 1 | 1 | 0 | 1 | 1 |
| D | 0 | 0 | 1 | 0 | 1 | 0 | 0 |
| J | 0 | 1 | 0 | 1 | 0 | 1 | 0 |
| C | 0 | 1 | 1 | 1 | 0 | 0 | 0 |
| D | 0 | 1 | 0 | 0 | 0 | 0 | 0 |
| F | 1 | 0 | 0 | 0 | 1 | 0 | 1 |
| H | 1 | 0 | 0 | 1 | 0 | 1 | 1 |
| J | 1 | 0 | 1 | 0 | 0 | 1 | 1 |
| C | 0 | 0 | 1 | 1 | 1 | 0 | 0 |
| E | 1 | 1 | 0 | 0 | 0 | 1 | 1 |
| I | 1 | 1 | 0 | 0 | 0 | 0 | 1 |
| K | 0 | 1 | 1 | 1 | 1 | 1 | 0 |
| D | 0 | 1 | 1 | 1 | 0 | 0 | 0 |
| J | 0 | 1 | 0 | 0 | 1 | 0 | 0 |

PROSTATE VOLUME: 23
SOURCE COUNT: 50

SOURCE ACTIVITY: 0.45 mCi
PRESCRIBED DOSE: 16000. cGY
ISOTOPE: I

FIG. 21

APPARATUS AND METHOD FOR DETERMINING OPTIMAL LOCATIONS TO PLACE RADIOACTIVE SEEDS AT A CANCEROUS SITE

MICROFICHE APPENDIX

A microfiche appendix consisting of 1 microfiche and 51 frames is included as part of the specification. A portion of the microfiche appendix contains material which is subject to copyright protection. The copyright owner has no objection to the facsimile reproduction by anyone of the material, as it appears in the United States Patent and Trademark Office files and records, but otherwise reserves all copyright in the material.

BACKGROUND

A) Field of Invention

The present invention relates to placing radioactive seeds at a cancerous site, and more particularly to a computer-program-implemented technique for determining optimal locations for placing radioactive seeds at a cancerous site.

B) Description of Related Art

At the present time there are many modalities of treatment for cancer. The most basic treatment is surgery. With this treatment modality, the cancerous site is simply excised by operative intervention. This treatment modality is ineffective when the cancerous site is not confined to a specific location, such as in the form of a tumor. Moreover, this treatment modality entails all of the risks and hazards associated with surgical procedures.

Another currently available treatment modality is external-beam radiation therapy. This treatment entails directing radiation beams from an external source to a cancerous site as an attempt to selectively kill the cancerous cells. There are also certain disadvantages of external-beam radiation therapy. One disadvantage is that this treatment kills healthy cells as well as cancerous cells. Also, with external-beam radiation therapy, the patient is required to visit a treatment center five days a week for a six week period.

Both the surgical and radiation treatment modalities are effective if performed at the early stages of the disease. When the disease has metastasized and is in its later stages, the treatment modality with the most promise is chemotherapy. With chemotherapy, agents are injected into the patient which can reach the distant metastatic sites. The agents are essentially toxins which are considered to be more toxic to the cancerous cells than to the normal cells.

Many physicians have also tried hormonal therapy as an adjunct to the surgical and radiation treatment modalities. For example, it is known that prostate cancer grows more rapidly in testosterone-rich environments. As such tumor shrinkage can be achieved by administering testosterone-suppressing hormones. However, hormonal therapy also has certain drawbacks. In particular, although many cancerous cells may die in a testosterone-deprived environment, some tumor cells may continue to thrive. Also, when hormonal therapy is used as a treatment for prostate cancer, a loss of sexual interest may result.

Cryosurgery has also been used for the treatment of cancer. This treatment involves freezing the cancerous tumor. When treating prostate cancer with this technique, needles are inserted into the prostate under the guidance of transrectal ultrasound. Liquid nitrogen is then inserted into the needles and the prostate is cooled to −180 C. Unfortunately, test results concerning cryosurgery reveal that a 30–50% positive biopsy-rate generally occurs six months after surgery.

The treatment modality which is the focus of the current invention is brachytherapy. With brachytherapy, radioactive seeds are placed inside a patient at the cancerous site to provide a radiation therapy. The radiation treatment provided by brachytherapy is largely confined to the cancerous site. Thus, the likelihood of damaging healthy adjacent tissue is minimized.

During the decades before modern imaging techniques became available, treatment with brachytherapy required implanting radioactive seeds by performing an operative procedure on the patient. Modern brachytherapy is, however, often based on less invasive approach. For example, modern brachytherapy treatment for prostate cancer is typically based on ultrasound imaging by using a technique generally known as transrectal ultrasound (TRUS) brachytherapy.

Referring to FIG. 1, conventional TRUS brachytherapy techniques typically require the use of a rectal ultrasound transducer 1, a radiation therapy ultrasound unit 9, and a treatment planning computer 12. As shown in FIG. 2, the transducer 1 includes a probe 3 which is inserted into the rectum and a template 5. The template 5, as shown in FIG. 3, includes a number of holes 8 into which needles 7 are placed. The holes 8 are arranged in a matrix which is defined by rows 0 through 12 and columns A through M. The needles 7, which are hollow, will ultimately be used for placing the radioactive seeds into the prostate.

The transducer 1 captures a series of parallel cross-sectional images of the prostate. Each cross-sectional image captured by the transducer is generally spaced at an interval of 5 mm from the preceding image. For most patients, six to nine images are required to scan the entire prostate. The radiation therapy ultrasound unit 9 contains a screen 11 which shows each of the cross-sectional images of the prostate captured by the transducer 1. A hard copy of each image can be made for treatment planning purposes.

FIG. 4 shows a detailed version of one of the images displayed on the screen 11. The dots shown on the image correspond to the holes 8 in the template 5 where the needles 7 to be used for implanting the radioactive seeds can be inserted. Similar to the template 5, the dots reflect a matrix which is defined by rows 0 through 12 and columns A through M. The vertical and horizontal spacing of the dots is 5 mm.

The radiation therapy ultrasound unit 9 calculates the volume of the prostate based on the measurements contained on each of the cross-sectional images captured by the transducer 1. After this volume is calculated, a physicist then determines a given number, location, and activity of radioactive seeds needed to effectively treat the prostate. This determination is based solely on intuition and experience. The determined number, location and activity of radioactive seeds are then loaded into a treatment planning computer 12. The computer 12 then generates isodose contours based on the number, location, and activity of radioactive seeds for each of the cross-sectional ultrasound images.

FIG. 5 shows a typical set of isodose contours which were generated by the computer 12 and superimposed over the ultrasound image shown in FIG. 4. The outer contour line 13 encloses an area of the prostate which will receive at least 50% of the prescribed radiation dose. The middle contour line 15 encloses an area of the prostate which will receive at least 100% of the prescribed radiation dose. And, the inner multiple contour lines 17 enclose areas of the prostate which will receive at least 150% of the prescribed radiation dose.

The physicist then compares the shape of the isodose contours in FIG. 5 with the prostate contour for each cross-sectional image. The objective of the treatment is to have the isodose contour 15 conform to the shape of the prostate to the highest degree possible. That is, the radiation produced by the seeds should have a minimal encroachment on areas outside the prostate. Also, the physicist must review those portions of the prostate which will receive more than 150% of the prescribed radiation dose to ensure that the patient is not overdosed.

Typically, the physicist has to refine the original prescription several times to generate an acceptable treatment plan. In most instances, it takes numerous iterations and a substantial amount of time to develop an acceptable treatment plan.

Once an acceptable treatment plan is developed, an appropriate number of radioactive seed are placed in needles 7 which are positioned in the appropriate holes within the template. The seeds are then inserted into the patient's prostate and the procedure is complete.

While conventional TRUS brachytherapy has proven to be effective in the treatment of prostate cancer, serious problems persist with this treatment modality. Specifically, conventional TRUS brachytherapy generally requires scanning the patient for ultrasound images on two separate occasions—on a first occasion for obtaining a pretreatment plan and, on a second occasion during which the radioactive seeds are actually implanted.

Given that ultrasound imaging is dependent on the exact position of the transducer 1, the images that a clinician acquires during the pretreatment procedure may differ dramatically from the images acquired during actual implantation procedure. Thus, the treatment plan which is designed to conform to the prostate boundaries formed on the pretreatment images may not conform very well to the images acquired at the time of implantation. This inability to reproduce images during the implantation procedure which are substantially the same as the images formed during the pretreatment procedure results in gross inefficiencies and sub-optimal treatment.

Another difficulty with conventional TRUS brachytherapy for treating prostate cancer is the inability to implement the pretreatment plan. Specifically, ultrasound images obtained for conventional pretreatment plans do not indicate where boney structures are located in relationship to the needle entry points. As a result, in many instances, a needle entry position defined by the pretreatment plan is blocked by a boney structure.

Also, even if TRUS brachytherapy for treating prostate cancer is performed with a conventional treatment planning system by conducting only a single session at the time of implantation and without conducting a pretreatment session, there are still certain drawbacks. In particular, after the prostate volume is measured by the system described above, a prescribed number and location of the radioactive seeds still needs to be determined.

With conventional treatment techniques, this prescription is based on intuition and experience and requires many iterations and thus a large amount of time to develop. Moreover, in many instances, the final prescription may not result in an optimal placement of the seeds. When this occurs, the prostate does not receive the appropriate radiation dose.

In view of these problems, there currently exits a need for a device or method that would allow a clinician to conduct TRUS brachytherapy for prostate cancer only at the time of implantation and in such a manner that the number and location of radioactive seeds will be quickly and precisely determined to optimize the radiation therapy.

OBJECTS AND SUMMARY OF THE INVENTION

It is therefore an object of the present invention to to develop a TRUS brachytherapy technique for treating cancer which can be administered on a single occasion to eliminate the need for pretreatment plan.

It is an additional object of the invention to develop a TRUS brachytherapy technique for treating cancer which determines the optimal location for placing the radioactive seeds at the cancerous site in a quick and automated manner.

In accordance with one aspect of the invention, a method is defined for determining optimal locations for placing radioactive seeds at a cancerous prostate, where the method comprises the steps of: (a) obtaining a plurality of cross-sectional images of the prostate; (b) tracing a contour of an area on each cross-sectional image of the prostate obtained from step (a); (c) transferring the contour and area of each cross-sectional image of the prostate defined in step (b) to a three-dimensional coordinate system; (d) defining a population of locations within each area of each cross-sectional image of the prostate where radioactive seeds can be placed; (e) defining a location of the urethra within each area of each cross-sectional image of the prostate; (f) using a genetic algorithm to determine an optimal number of locations within the prostate to place the radioactive seeds; (g) determining radiation levels within the prostate based on the optimal number of locations defined by step (f); (h) identifying portions of the prostate which receive various levels of a prescribed radiation dose; (i) displaying contours on each cross-sectional image of the prostate which show the portions defined in step (h); and (j) producing a treatment plan showing the optimal number of locations within the prostate where the radioactive seeds are to be placed.

In accordance with another aspect of the invention, an apparatus for determining optimal locations for placing radioactive seeds at a cancerous prostate defined, where the apparatus comprises: (a) means for obtaining a plurality of cross-sectional images of the prostate; (b) means for tracing a contour of an area on each cross-sectional image of the prostate obtained from means (a); (c) means for transferring the contour and area of each cross-sectional image of the prostate defined by means (b) to a three-dimensional coordinate system; (d) means for defining a population of locations within each area of each cross-sectional image of the prostate where radioactive seeds can be placed; (e) means for defining a location of the urethra within each area of each cross-sectional image of the prostate; (f) means for using a genetic algorithm to determine an optimal number of locations within the prostate to place the radioactive seeds; (g) means for determining radiation levels within the prostate based on the optimal number of locations defined by means (f); (h) means for identifying portions of the prostate which receive various levels of a prescribed radiation dose; (i) means for displaying contours on each cross-sectional image of the prostate which show the portions defined in step (h); and (j) means for producing a treatment plan showing the optimal number of locations within the prostate where the radioactive seeds are to be placed.

In accordance with still another aspect of the present invention, a method for determining optimal locations for placing radioactive seeds at a cancerous site is defined, where the method comprises the steps of: (a) obtaining a plurality of cross-sectional images of the cancerous site; (b) tracing a contour of an area on each cross-sectional image of the cancerous site obtained from step (a); (c) transferring the contour and area of each cross-sectional image of the cancerous site defined by step (b) to a three-dimensional coordinate system; (d) defining a population of locations within each area of each cross-sectional image of the cancerous site where radioactive seeds can be placed; and, (e) using a genetic algorithm to determine an optimal number of locations within the cancerous site to place the radioactive seeds.

In accordance with yet another aspect of the inventions, an apparatus for determining optimal locations for placing radioactive seeds at a cancerous site is defined, where the apparatus comprises: (a) means for obtaining a plurality of cross-sectional images of the cancerous site; (b) means for tracing a contour of an area on each cross-sectional image of the cancerous site obtained from means (a);(c) means for transferring the contour and area of each cross-sectional image of the cancerous site defined by means (b) to a three-dimensional coordinate system; (d) means for defining a population of locations within each area of each cross-sectional image of the cancerous site where radioactive seeds can be placed; and, (e) means for using a genetic algorithm to determine an optimal number of locations within the cancerous site to place the radioactive seeds.

BRIEF DESCRIPTION OF THE DRAWINGS

The accompanying drawings are included to provide an understanding of the invention and constitute a part of the specification.

DETAILED DESCRIPTION OF THE INVENTION

Figure 6:
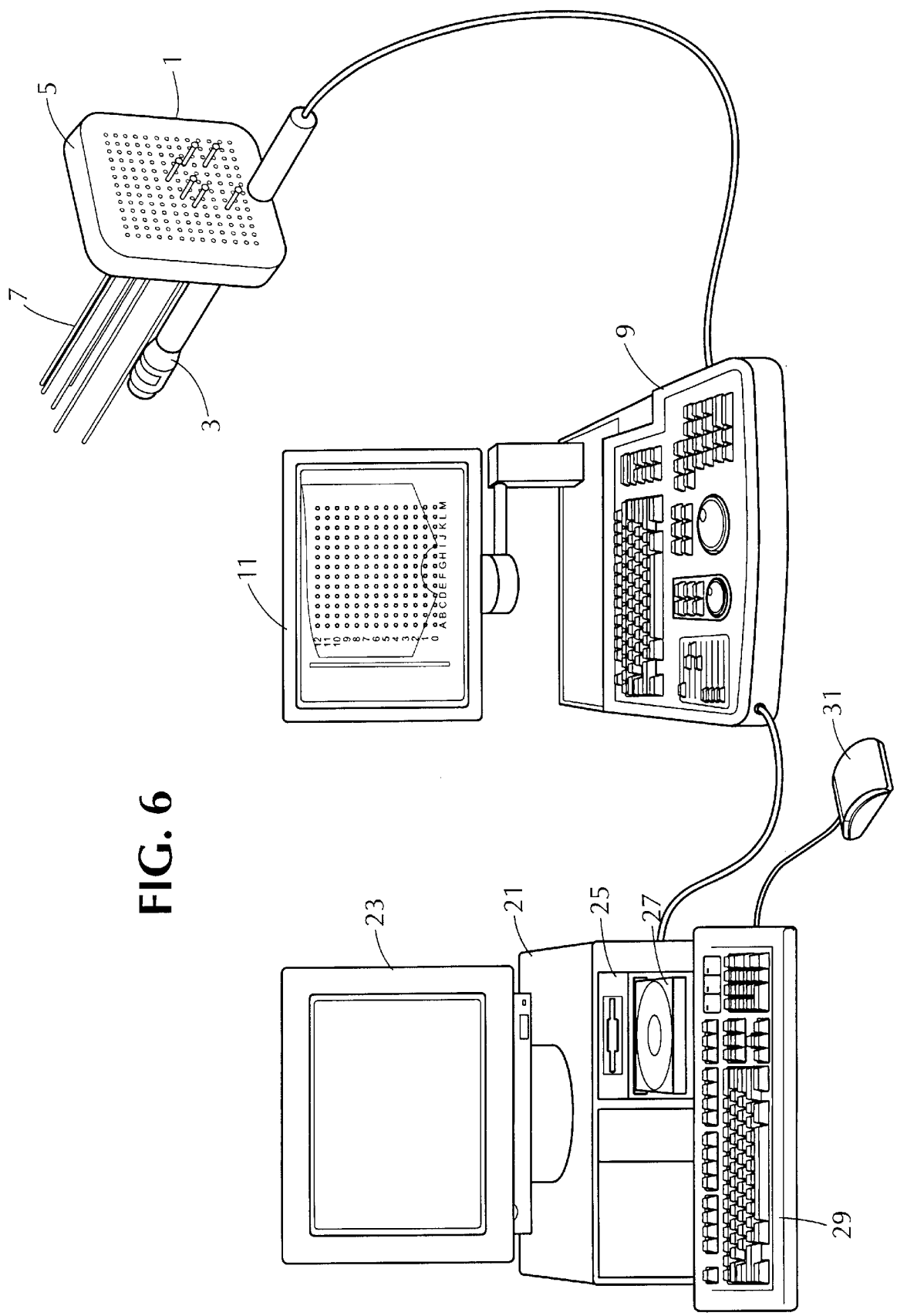
FIG. 6 illustrates a system used for determining optimal locations to place radioactive seeds at a cancerous site in accordance with the present invention.

FIG. 6 shows a system for determining optimal locations to place radioactive seeds at a cancerous site in accordance with present invention. The system includes a rectal ultrasound transducer 1, a radiation therapy ultrasound unit 9, and a radiation optimization unit 21.

The transducer 1 is connected to the unit 9 in a manner similar to that of conventional devices such that a picture of each cross-sectional image of the prostate captured by the transducer 1 is displayed on the screen 11. Each cross-sectional image displayed on the screen 11 is stored on a disc drive contained in the optimization unit 21, as is known in the art, by using image acquisition software. The optimization unit 21 then analyses the cross-sectional images of the prostate to determine optimal locations for placing radioactive seeds within the prostate.

The optimization unit 21 is a portable computer which typically includes a Pentium central processing unit, a 32MB random access memory, a built-in monitor which is designated by reference numeral 23, a 1.44MB floppy disk drive which is designated by reference numeral 25, a hard drive, a CD ROM which is designated by reference numeral 27, a keyboard which is designated by reference numeral 29, a mouse which is designated by reference numeral 31, and Microsoft's Windows 95 operating system.

In an alternative embodiment of the invention, a lap top personal computer can be used as the optimization unit 21.

The optimization unit 21 also includes a Fortran-90 compiler and an optimization computer program which is written in Fortran. The optimization computer program analyzes each of the cross-sectional areas captured by the transducer 1 to determine the optimal locations for placing radioactive seeds within the prostate. The optimization computer program includes nine modules to determine the optimal locations for placing radioactive seeds.

A description of each these modules is provided below with reference to the drawings and Appendices of this application. For purposes of discussing each of the software modules, it is assumed that seven cross-sectional images of the prostate, which are spaced 5 mm apart, were obtained by the transducer 1. In the discussion, Level 0 will define the most superior cross-sectional image (i.e., the image positioned highest in the body), and Level 6 will define the most inferior image (i.e., the image positioned the lowest in the body).

MODULE 1

Figure 7:
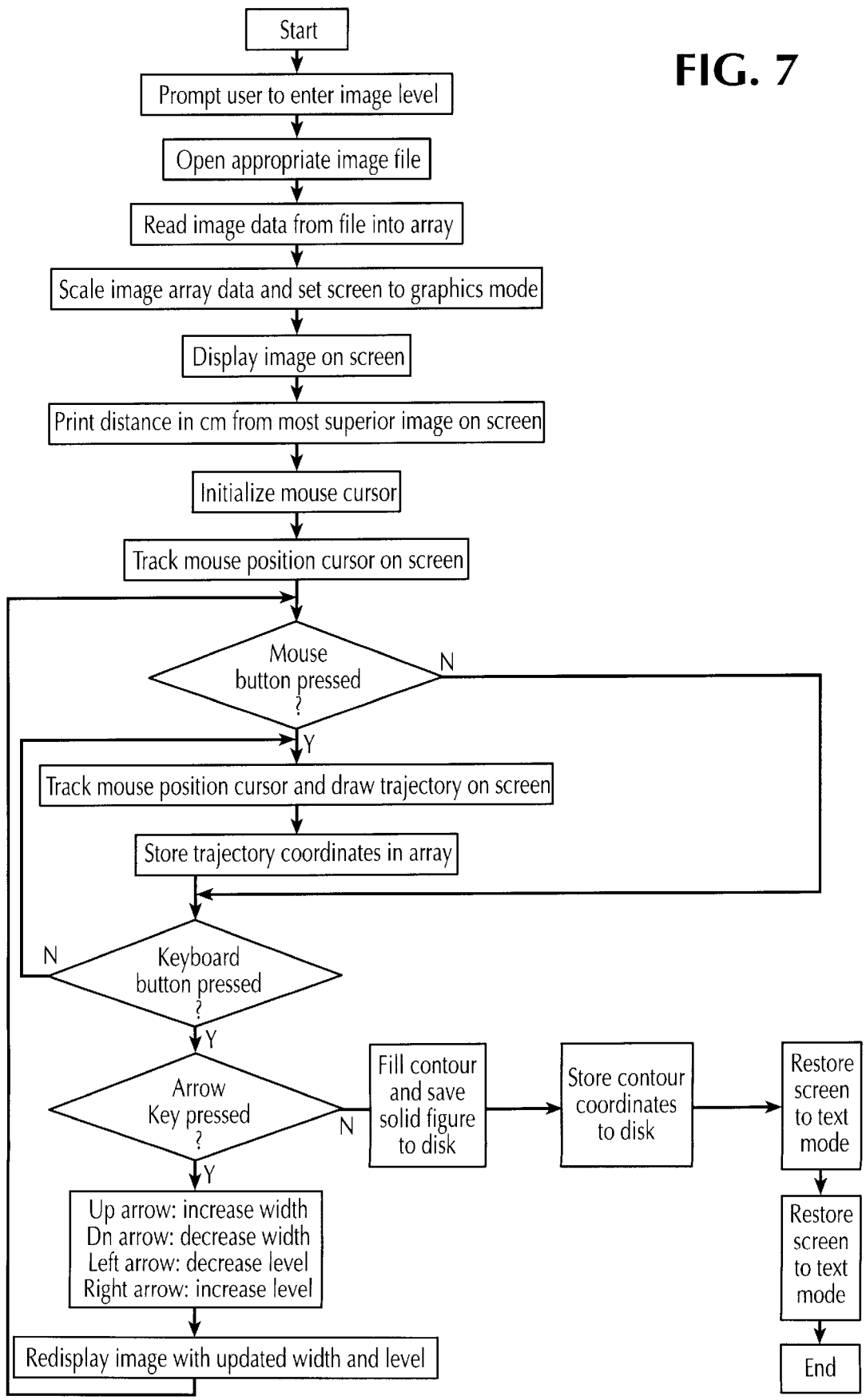
FIG. 7 illustrates a flow chart describing Module 1 of a computer program used by the system shown in FIG. 6.

Module 1 of the optimization computer program is known as the contour generator module. A flow chart describing Module 1 is shown in FIG. 7, whereas, a listing of the source code is provided in Appendix 1 of the microfiche submitted herewith.

Figure 8:
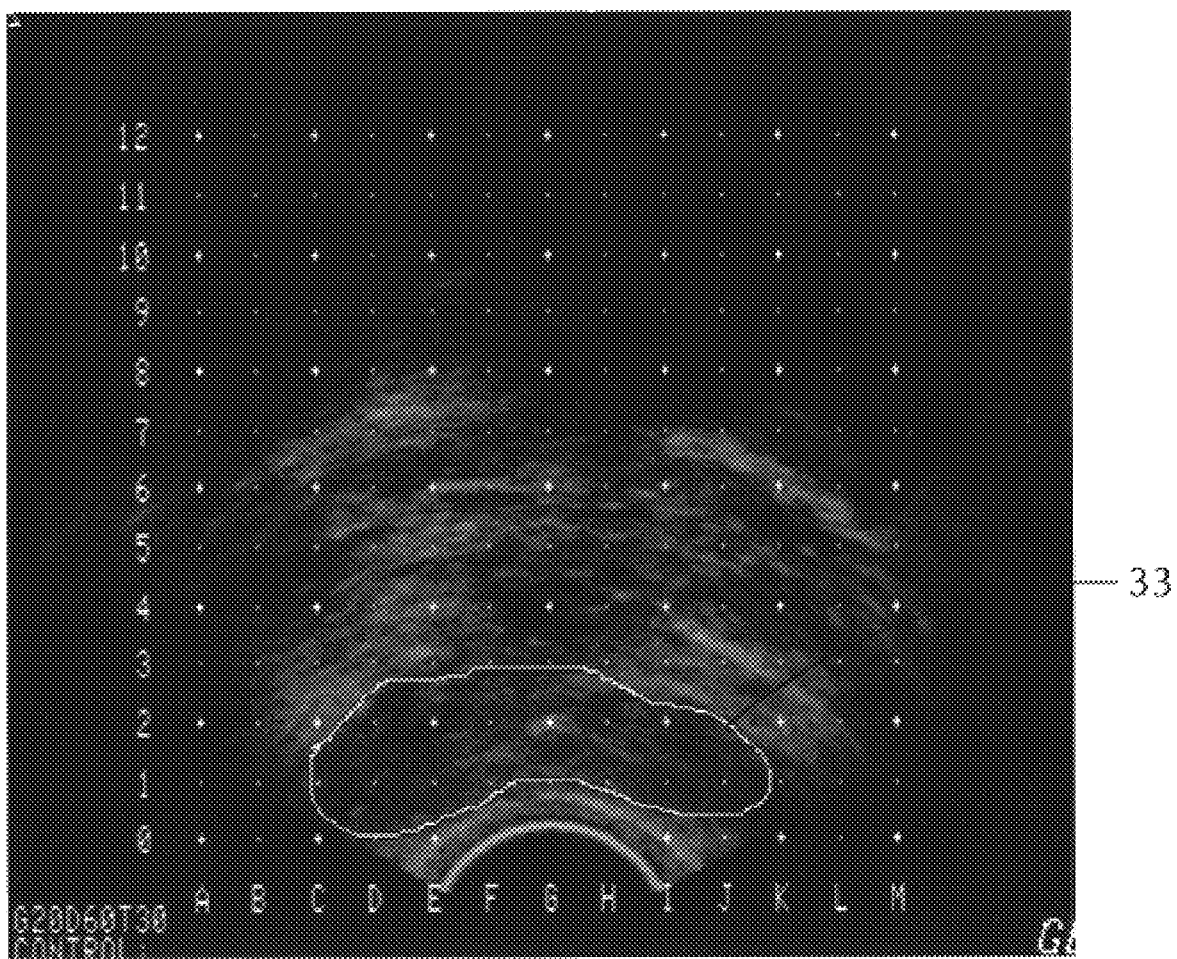
FIG. 8 illustrates an image displayed on a screen of the system shown in FIG. 6.

Referring to FIG. 8, Module 1 is the program that is used for tracing a prostate contour 33 on each of the cross-sectional images captured by the transducer 1. In particular, this module allows an operator to trace the contour 33 on the screen 23 of the optimization unit 21 with the aid of the mouse 31. After the contour 33 is drawn, the operator presses one of the keys on the keyboard 29. This process occurs for each of the images defined by Levels 0 through Level 6.

Two files are stored to the hard drive of the optimization unit 21 after the contour 33 is traced for each of the Levels. Specifically, for each contour 33 which is traced, a first file defining the coordinates of the contour 33 and a second file defining a solid Region-of-Interest (ROI) within the contour 33 are written to the hard drive of the optimization unit 21.

These files are named according cross-section image they represent. For example, after the contour 33 for Level 0 is captured, the coordinates of the contour 33 are stored in a file labeled "cont0.dat." Similarly, after the data defining the ROI for Level 0 is captured, the data is stored in a file called "ROI0.dat."

A corresponding process occurs for each image at the other levels. That is, the coordinates for the contour of Level 4 are stored in a file called "cont4.dat" and the data defining the ROI for Level 4 is stored in a file called "ROI4.dat."

Module 1 of the optimization program also provides windowing and leveling features. The windowing feature allows the operator to alter the gray scale width of the displayed image, whereas, the leveling feature allows the user to change the gray scale level of the image by using the arrow keys on the keyboard 29. The windowing and leveling features are similar to those implemented on CT and MRI scanners.

MODULE 2

Figure 9:
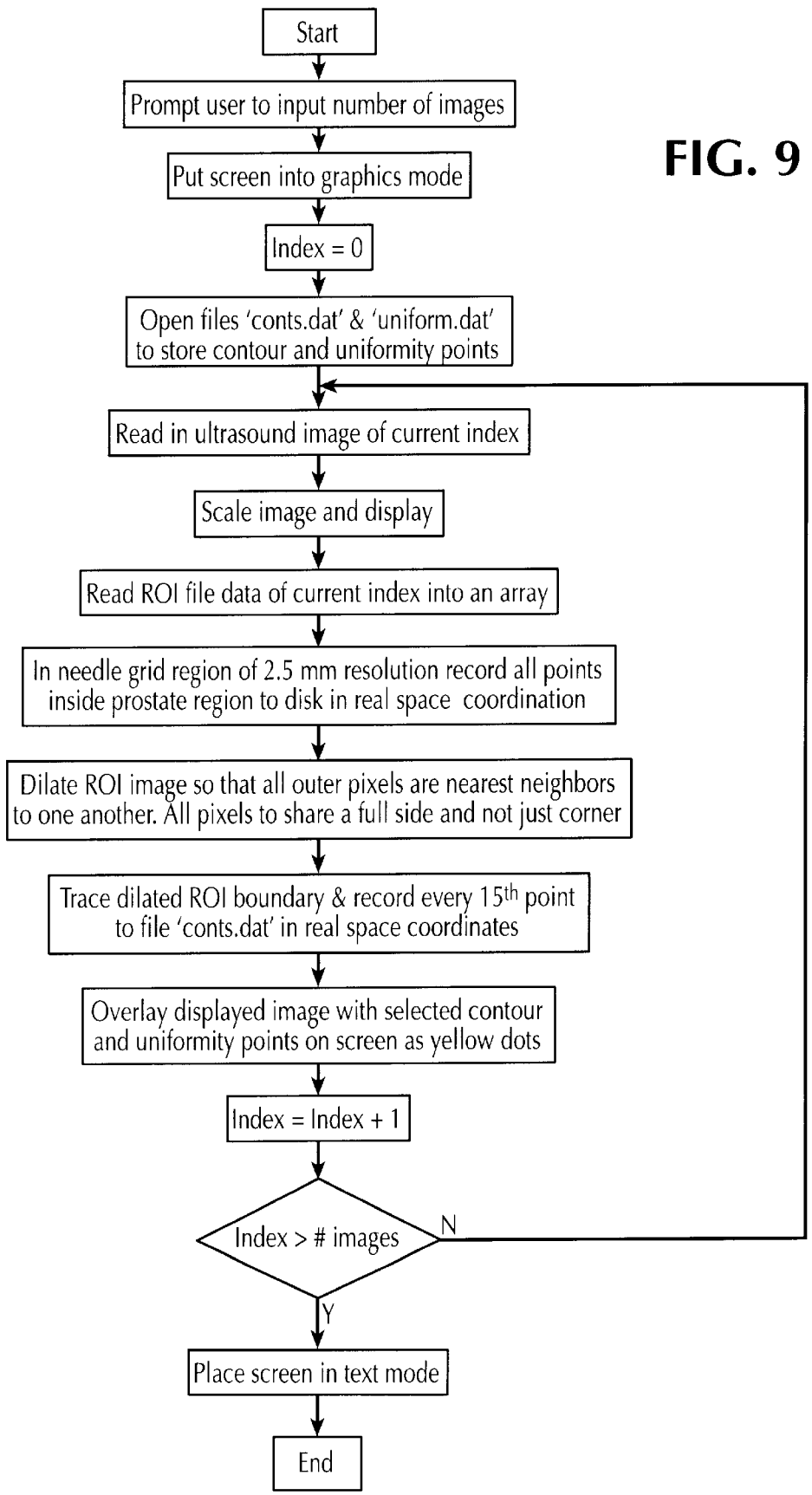
FIG. 9 illustrates a flow chart describing Module 2 of the computer program used by the system shown in FIG. 6.

Module 2 of the optimization computer program is known as a contour and uniformity point generator and is provided to convert the data captured by Module 1 to a three dimensional coordinate system. A flow chart describing Module 2 is shown in FIG. 9, whereas, a listing of the source code is provided in Appendix 2 of the microfiche submitted herewith.

The data captured by Module 1 was stored in pixel format (i.e., a format defined by 480 rows and 640 columns). Thus, to allow for meaningful quantitative calculations to be performed based on the data, it is necessary to convert the data to a three dimensional coordinate system. Module 2 performs this conversion. In particular, Module 2 automatically reads the ROI data files generated for each of the levels captured by Module 1 and performs two conversions based on this data.

Figure 10:
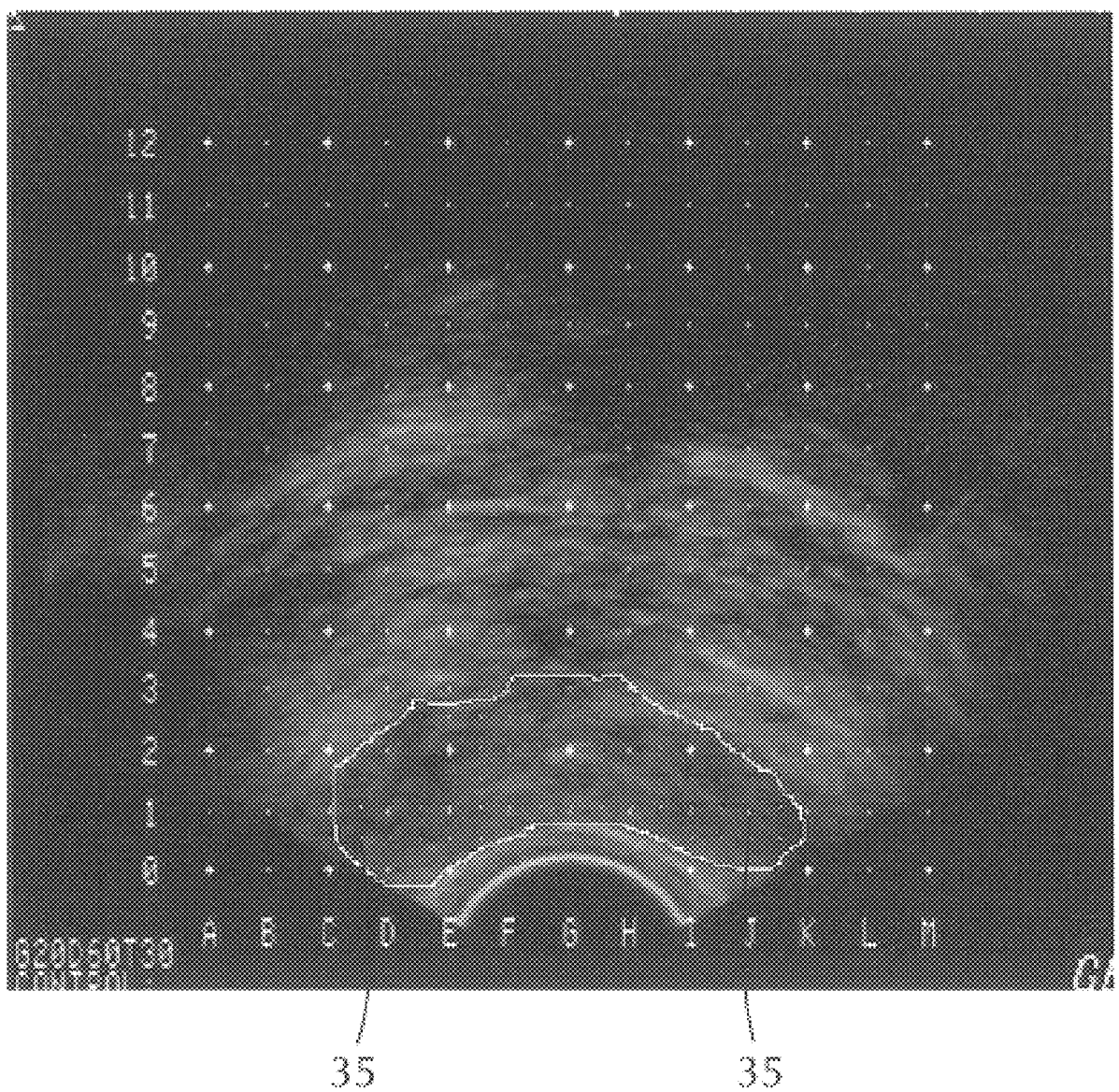
FIG. 10 illustrates an image displayed on the screen of the system shown in FIG. 6.

First, Module 2 traces the prostate contour from the solid ROI image captured for each Level in Module 1 and stores every $15^{th}$ coordinate point on the boundary in a real space coordinate system to a file called "conts.dat." Here, unlike Module 1, the coordinate points of the contour for each level are stored in one file. Secondly, Module 2 defines real space coordinate points, at 2.5 mm increments, for every point lying inside the ROI for every level. Similarly, this data is recorded for each level and stored to one file called "uniform.dat." FIG. 10 shows an example of the real space coordinate points 35 derived by Module 2 for every point lying within an ROI at one of the levels.

It is noted that Module 2 arbitrarily defines contours by using every $15^{th}$ data point and ROI's by using 2.5 mm increments. Module 2 can alternatively be designed to define the data points and increments differently to achieve a greater degree of resolution. For example, Module 2 could define the contours by using every $5^{th}$ data point and define the ROI's by using 0.5 mm increments. However, using more resolved increments such as these results in data processing delays. Given that the optimization unit 21 is used a real-time environment (i.e., when a procedure is being performed on a patient), in most instances such a delay is considered to be problematic.

MODULE 3

Figure 11:
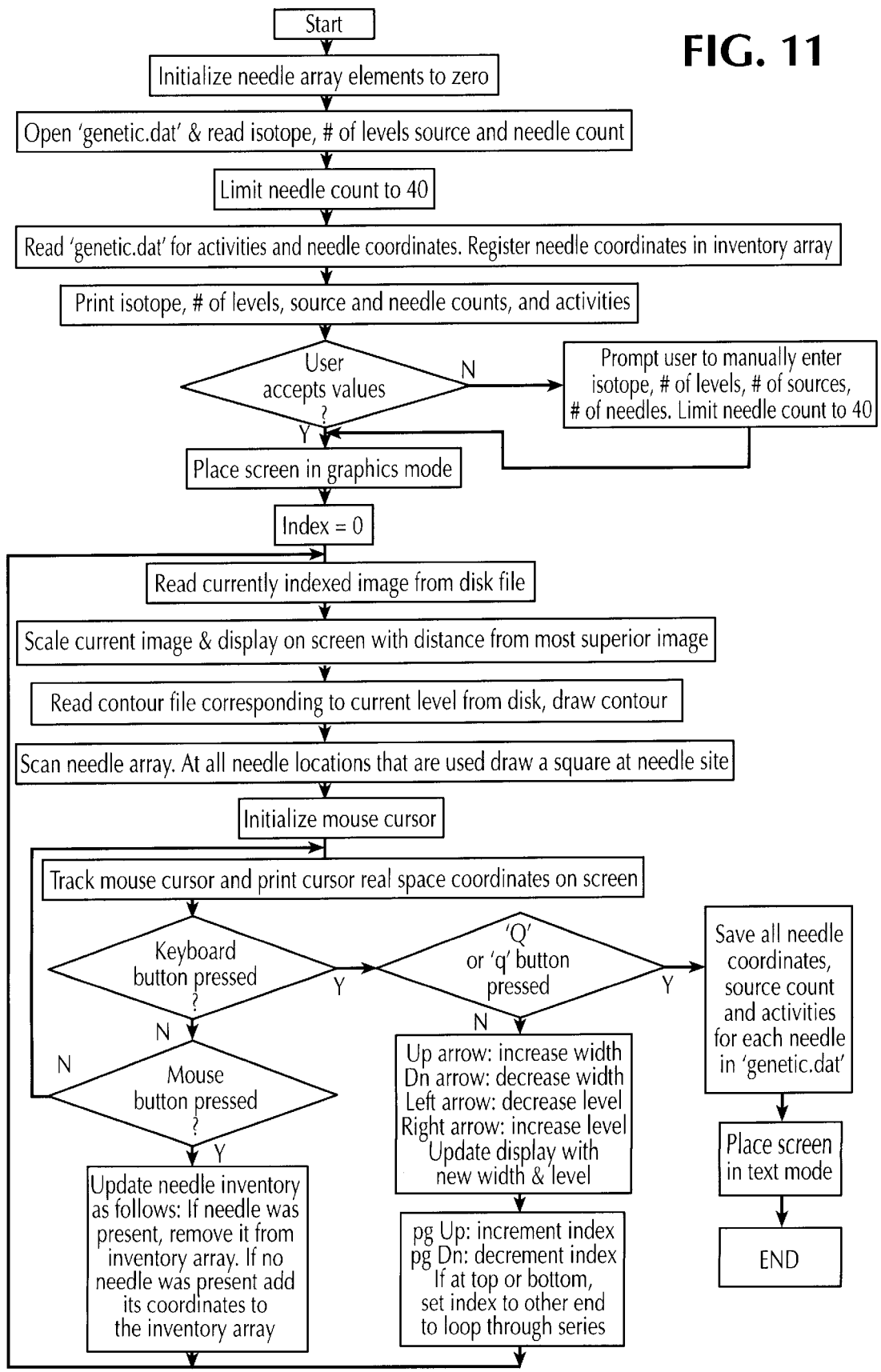
FIG. 11 illustrates a flow chart describing Module 3 of the computer program used by the system shown in FIG. 6.

Module 3 of the optimization computer program is known as the needle entry implementation module. A flow chart describing Module 3 is shown in FIG. 11, whereas, a listing of the source code is provided in Appendix 3 of the microfiche submitted herewith.

Module 3 is used for entering the coordinates of the needles 7 that will be used to insert the radioactive seeds into the patient. The coordinates of the needles 7 that will ultimately be used are defined solely by the intuition of the operator of the optimization unit 21. The operator defines these coordinates by taking into account the various factors such as the shape of the prostate and the bone structure of the patient.

Module 3 begins by displaying the Level 0 ultrasound image. The operator then either adds or deletes a needle location by moving the mouse cursor to the desired location and clicking the mouse button 31. If a needle is present at the cursor site, the needle can be deleted. Conversely, if a needle is not present at the cursor site a needle can be added at the site.

Figure 12:
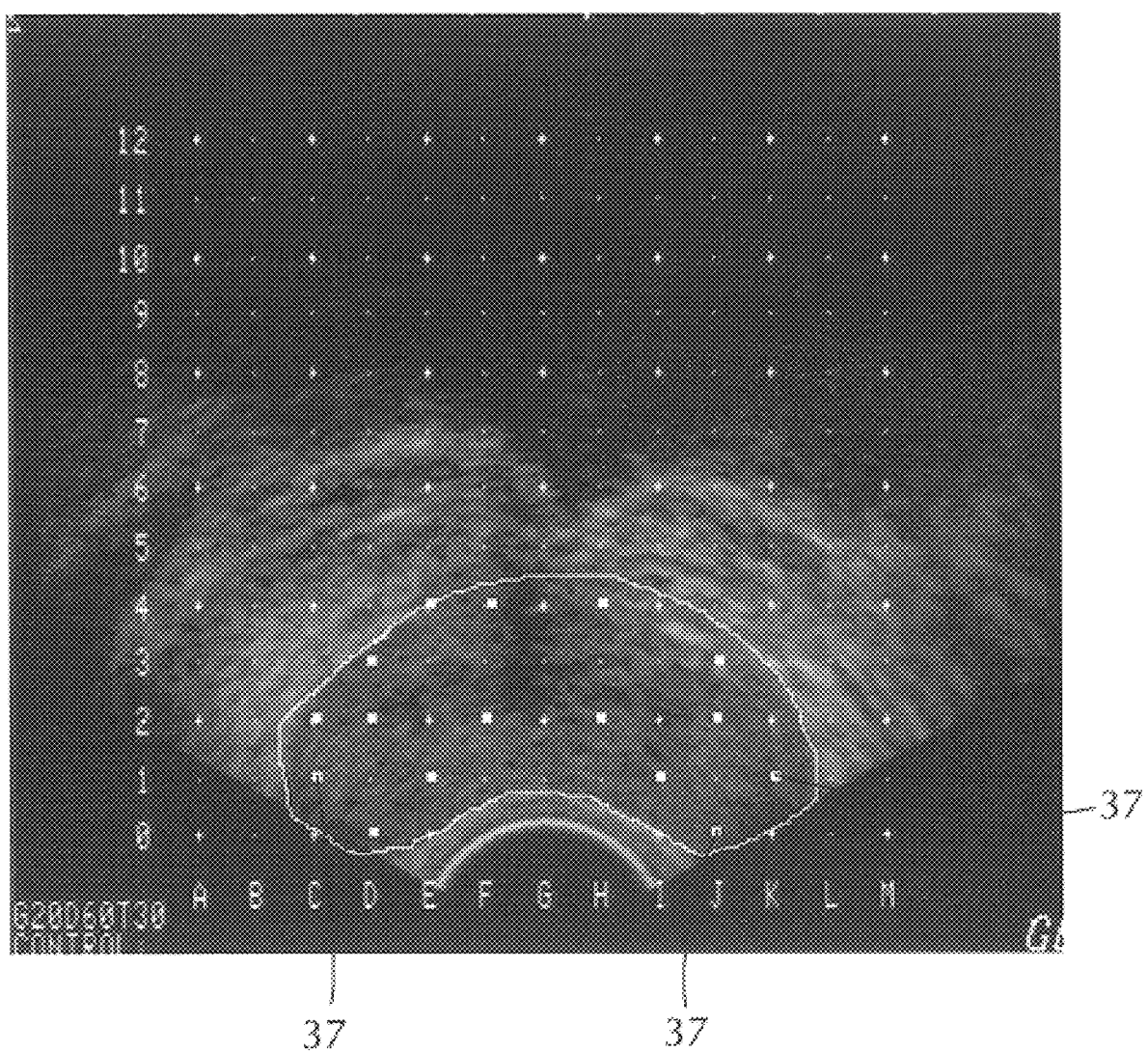
FIG. 12 illustrates an image displayed on the screen of the system shown in FIG. 6.

FIG. 12 shows an example of a screen after the operator has defined the coordinates for placing the needle sites. Referring to FIG. 12, the needle sites are indicated by a small squares 37 which are superimposed on the ultrasound image. As mentioned above, clicking the mouse button 31 either adds or deletes a needle.

The windowing and leveling capabilities implemented in the module are accessed by the arrow keys. The 'page up' and 'page down' keys are used to scroll through each image Level obtained for the patient. When the user presses the 'q' key the needle coordinates are stored in a file called "genetic.dat" and the program terminates.

MODULE 4

Figure 13:
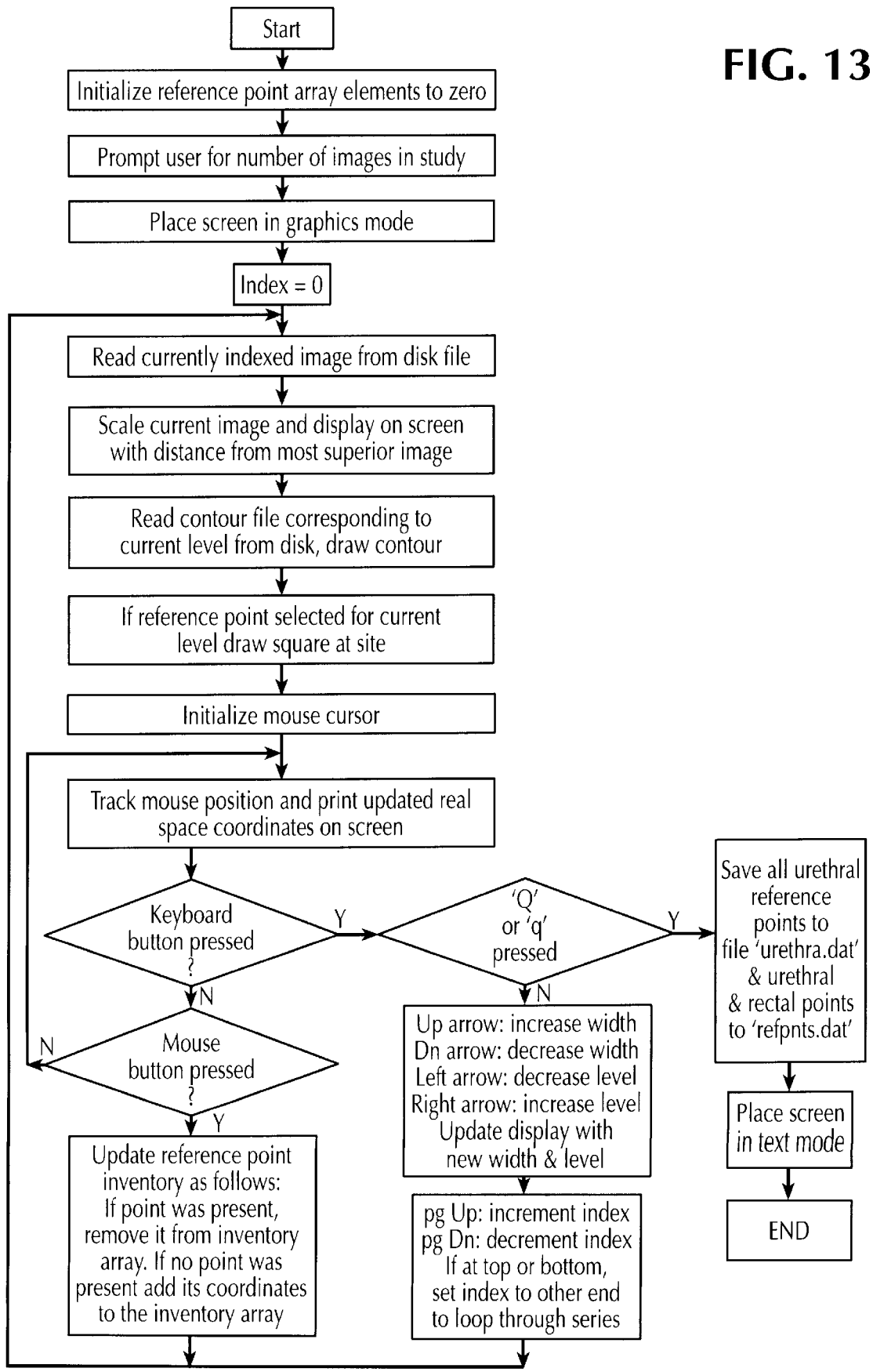
FIG. 13 illustrates a flow chart describing Module 4 of the computer program used by the system shown in FIG. 6.

Module 4 of the optimization computer program is known as the urethral reference point entry module and is used to define the location of the urethra relative to the prostrate. A flow chart describing Module 4 is shown in FIG. 13, whereas, a listing of the source code is provided in Appendix 4 of the microfiche submitted herewith.

Figure 14:
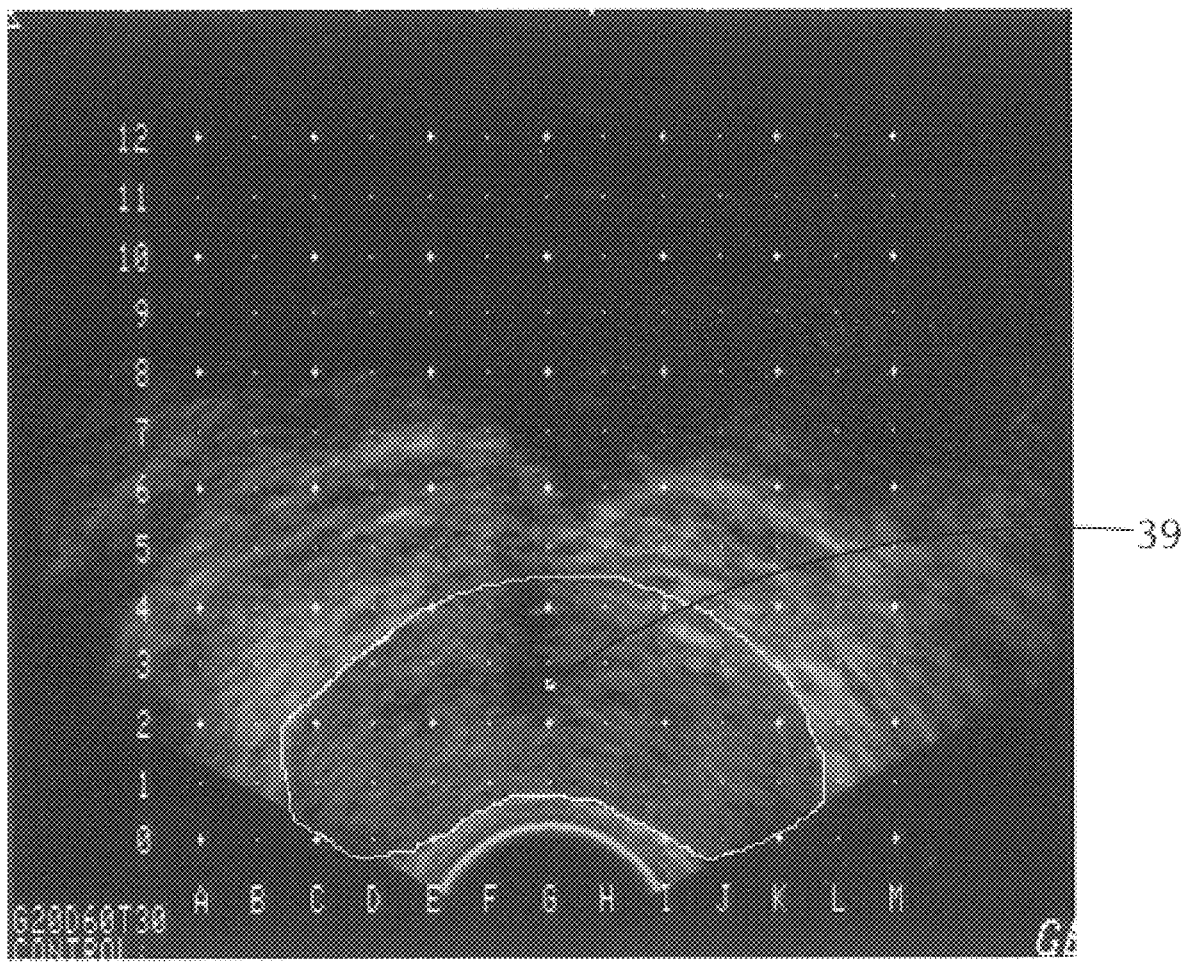
FIG. 14 illustrates an image displayed on the screen of the system shown in FIG. 6.

Module 4, which is similar to Module 3, begins by displaying the Level 0 ultrasound image. The operator defines the location of the urethra by moving the mouse cursor to the desired location and clicking the mouse button. Referring to FIG. 14, the urethra 39 is indicated by a small square which are superimposed on the ultrasound image.

Module 4 also provides windowing and leveling by use of the arrow keys and the 'page up' and 'page down' keys are similarly used to scroll through each image Level obtained for the patient. When the user presses the 'q' key the coordinates defining the location of the urethra for each level are stored in a file called "urethra.dat."

Module 4 also stores the urethral coordinates to a file called "refpnts.dat." The Module also stores the origin points of each image to be used as rectal reference points in "refpnts.dat." The rectal reference points are taken to be x=0, z=0 and y=(−0.5)*(Level #). For example, for Level 3 the rectal reference points are x=0, z=0, and y=−1.5.

MODULE 5

Module 5 of the computer program is the optimization module which is used to define the optimal locations for placing the radioactive seeds within the prostate. A flow chart describing Module 5 is shown in FIGS. 15A through 15F, whereas, a listing of the source code is provided in Appendix 5 of the microfiche submitted herewith.

The optimization module used by the present invention includes what is generally referred to in the art as a genetic algorithm. A genetic algorithm models the fundamental mechanisms of evolution and natural selection to arrive at an optimal solution to a problem. Specifically, in nature, characteristics of an organism are encoded in streams of DNA known as chromosomes. The chromosomes change over time, as a result of evolution and natural selection, to produce a superior organism.

In a genetic algorithm, the characteristics of potential solutions to a problem are similarly coded in symbol streams. The genetic algorithm then emulates evolution and natural selection by evaluating the fitness of populations of symbol streams to arrive at an optimal solution to a problem. The symbol streams are scored by an objective function. The higher the symbol stream scores, the more desirable the potential solution to the problem.

A genetic algorithm is typically initialized with a randomly chosen population of symbol streams. Each symbol stream is then scored by the objective function to identify which symbol streams will become parents to mate and generate a subsequent generation of symbol streams.

The parents of the subsequent generations are selected in a manner favoring higher scoring symbol streams. After the parents are selected, they are paired off and mated. In a process analogous to cross-over in biological reproduction, where a child's genetic composition is a combination of its parents, genetic algorithms interchange subsections of the each parent's symbol stream to form new members of the next generation. Genetic algorithms also randomly change a small number of data stream components in a process analogous to the evolutionary phenomenon of mutation.

An operation of the genetic algorithm designed in accordance with the present invention and implemented by Module 5 will now be described. Module 5 begins by prompting the operator for the prescribed radiation dose (e.g., 16000 cGy) which is to be used on the patient and the number of optimization generations desired by the operator. The module then retrieves the ROI files to determine whether or not each needle location previously defined by the operator in Module 3 falls within the prostate. The program then scans the selected needle sites on all levels in the study and makes an array of all needle sites found to be within the prostate. The program also reads the contour and uniformity points which will be used for evaluating the quality of the prospective treatment plans. The file 'genetic.dat' provides the program with the information regarding needle locations, source activities, the initial number of sources for the first generation of trial plans, as well as the number of images in the series.

Module 5 then uses a genetic algorithm that was developed in accordance with the present invention to optimize the quality of a proposed plan for treating the cancerous prostate with radioactive seeds. The basic steps of the genetic algorithm used by Module 5 include: (1) randomly selecting a population for symbol streams for the first generation; (2) evaluating each member of the population by applying the objective function; (3) using scores of the objective function as criteria to select individuals to act as parents for the next generation; (4) pairing off parents and mating the pairs by interchanging some of the symbols; (5) performing mutations on the newly created symbol streams; (6) replacing a symbol stream from step 5 with the highest scoring symbol stream of the previous generation to define a new generation of symbol streams; (7) evaluating each member of the new generation by applying the objective function; (8) repeating steps 3 through 7 until the desired generation count is reached; and (9) selecting the highest scoring stream.

The first step of the genetic algorithm used in accordance with the present invention involves randomly defining a number of treatment plans for each of the needle sites determined to be positioned within the prostate. Each randomly generated treatment plan is represented by strings of bit patterns. The bit patterns are stored in a global chromosome array. If a radioactive source is present at a site, the corresponding array location has a 1. If no radioactive source is present at the site, the corresponding array location has a 0.

Table 1 below shows a hypothetical population of bit streams generated by the genetic algorithm developed in accordance with present invention.

TABLE 1

POPULATION OF DATA STREAMS

|  | 1 | 1 | 0 | 1 | 1 | 0 | 1 | 1 | 0 | 1 | 0 |
|---|---|---|---|---|---|---|---|---|---|---|---|
|  | 2 | 0 | 0 | 1 | 1 | 0 | 0 | 1 | 1 | 0 | 1 |
|  | . | 1 | 1 | 0 | 0 | 1 | 0 | 0 | 1 | 1 | 1 |
|  | . | 0 | 0 | 1 | 1 | 1 | 0 | 0 | 1 | 1 |
|  | . | 0 | 1 | 0 | 0 | 1 | 1 | 1 | 1 | 0 | 0 |
|  | . | 1 | 0 | 0 | 1 | 1 | 0 | 0 | 1 | 1 | 1 |
|  | . | 1 | 1 | 0 | 1 | 0 | 1 | 0 | 0 | 1 | 0 |
|  | . | 0 | 1 | 0 | 0 | 1 | 1 | 1 | 0 | 0 | 1 |
|  | . | 0 | 0 | 1 | 1 | 1 | 0 | 0 | 1 | 0 | 0 |
|  | N | 1 | 1 | 1 | 0 | 0 | 1 | 0 | 0 | 1 | 1 |
| OVERALL SCORE OF OBJECTIVE FUNCTION | 24 | 15 | 10 | 27 | 12 | 18 | 9 | 14 | 30 | 11 |
| CUMULATIVE SCORE | 24 | 39 | 49 | 76 | 88 | 106 | 115 | 129 | 159 | 170 |

Numbers 1 through N represent the number of needle sites determined to be within the prostate for each data stream. For purposes of this discussion, in Table 1 it is assumed that 10 hypothetical needle sites (i.e., N=10) and 10 hypothetical data streams are used by the genetic algorithm developed in accordance with the present invention. However, in actuality, there are typically more than 100 needle sites contained within a data stream.

The second step of the genetic algorithm involves evaluating each data stream of the population by applying the objective function. Creating an objective function is the most critical aspect when designing a genetic algorithm. The objective function used in accordance with the present invention performs two calculations. First, the objective function calculates the radiation dose at each contour, uniformity, urethral and rectal point for each data stream.

Then, the objective function determines an overall score based on the weighted sum of three specific scores which evaluate the radiation dose of the rectum, urethra, and prostate. These three scores are hereinafter referred to as the rectal score, the urethral score, and the prostate score.

Figure 15A:
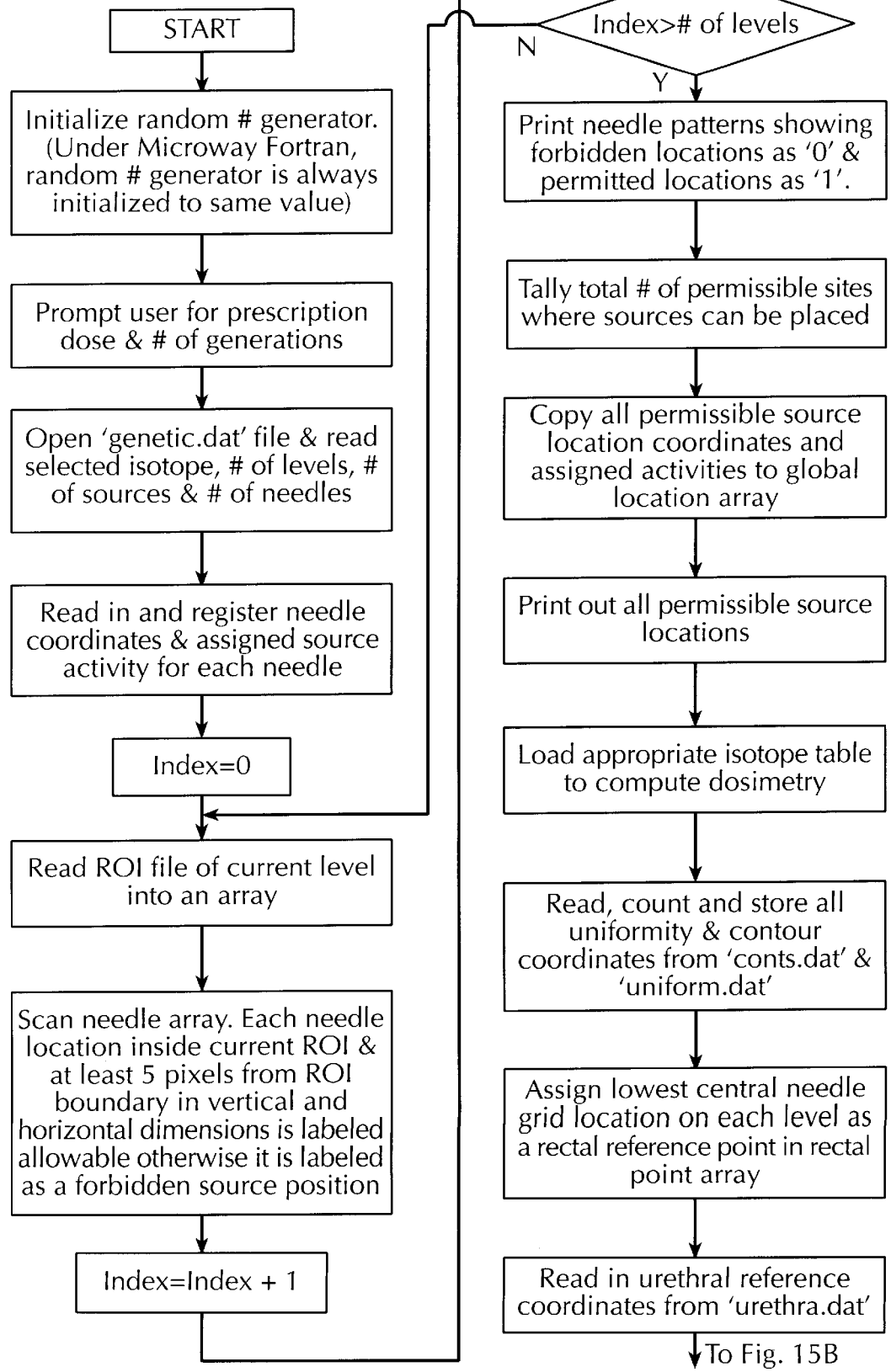
FIGS. 15A through 15F illustrate flow charts which describe Module 5 of the computer program used by the system shown in FIG. 6.
Figure 15B:
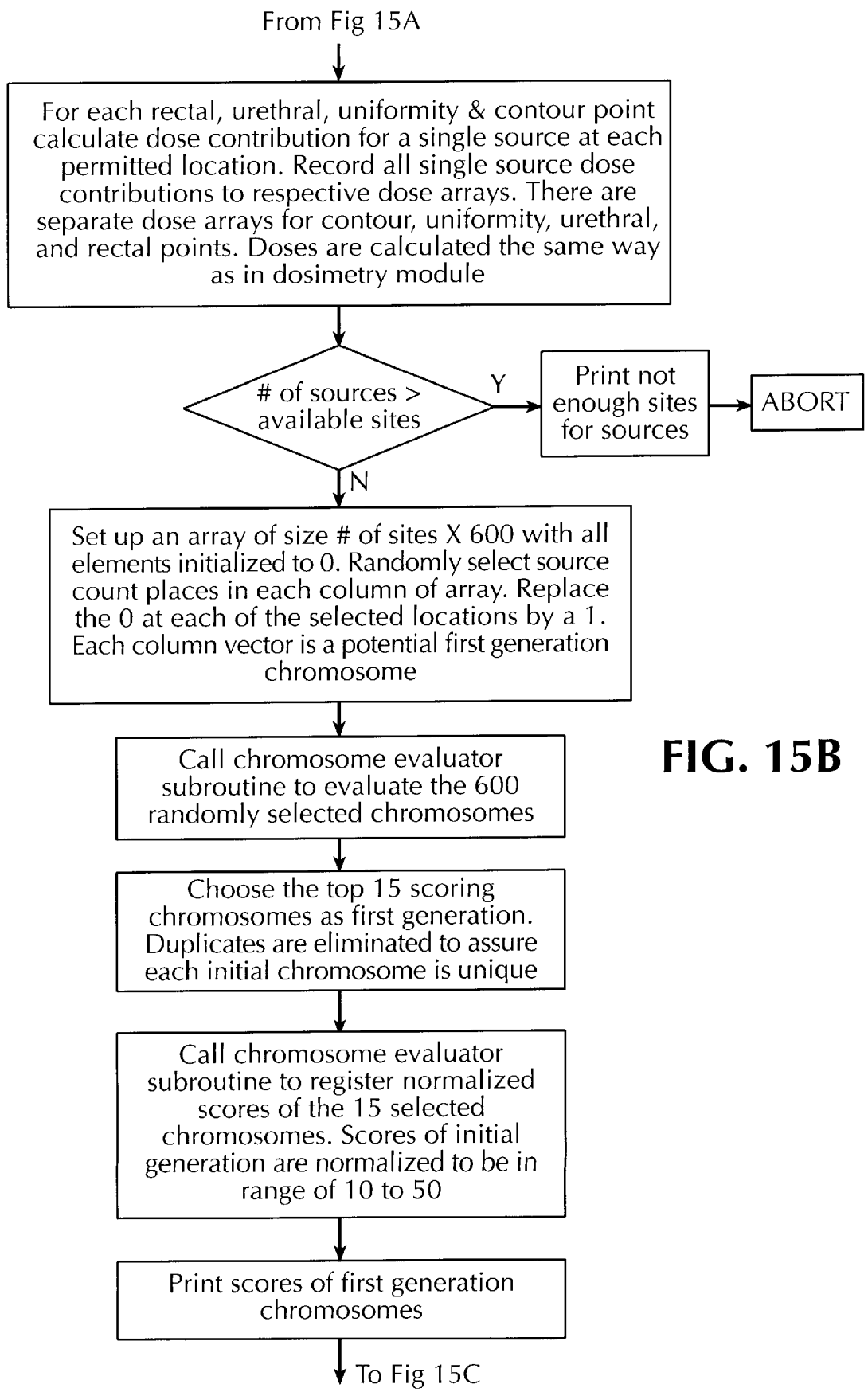
Figure 15C:
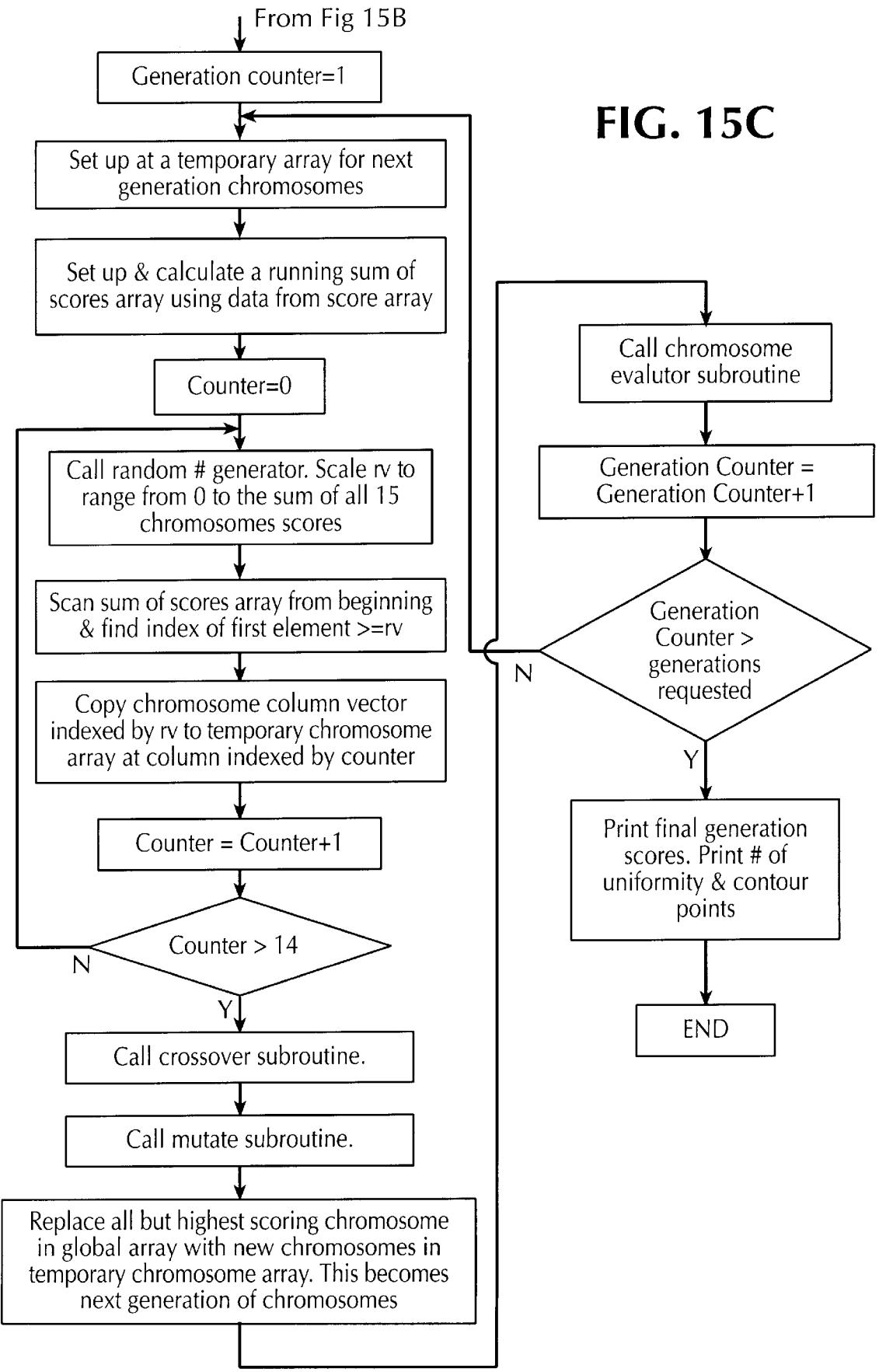
Figure 15D:
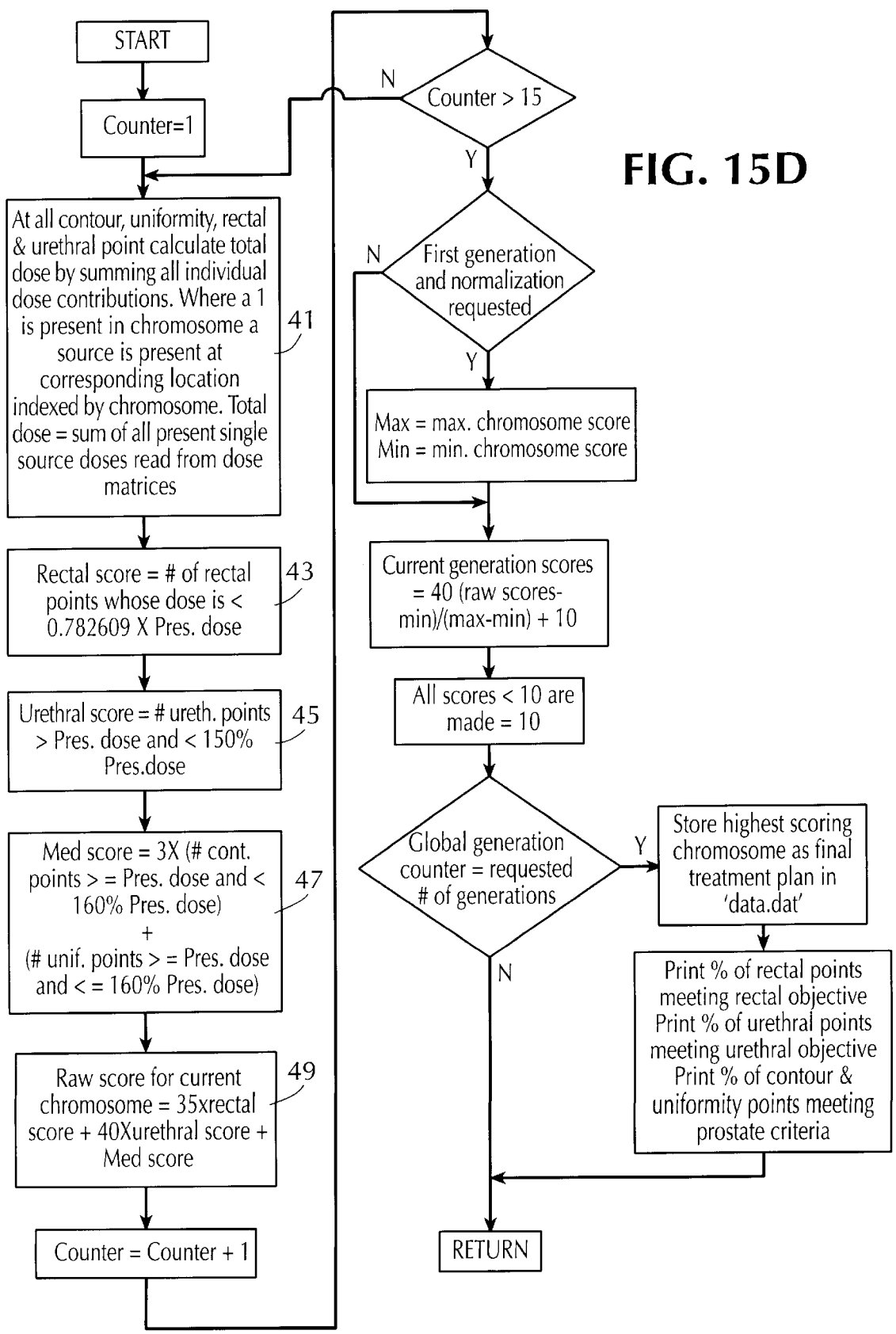
Figure 15E:
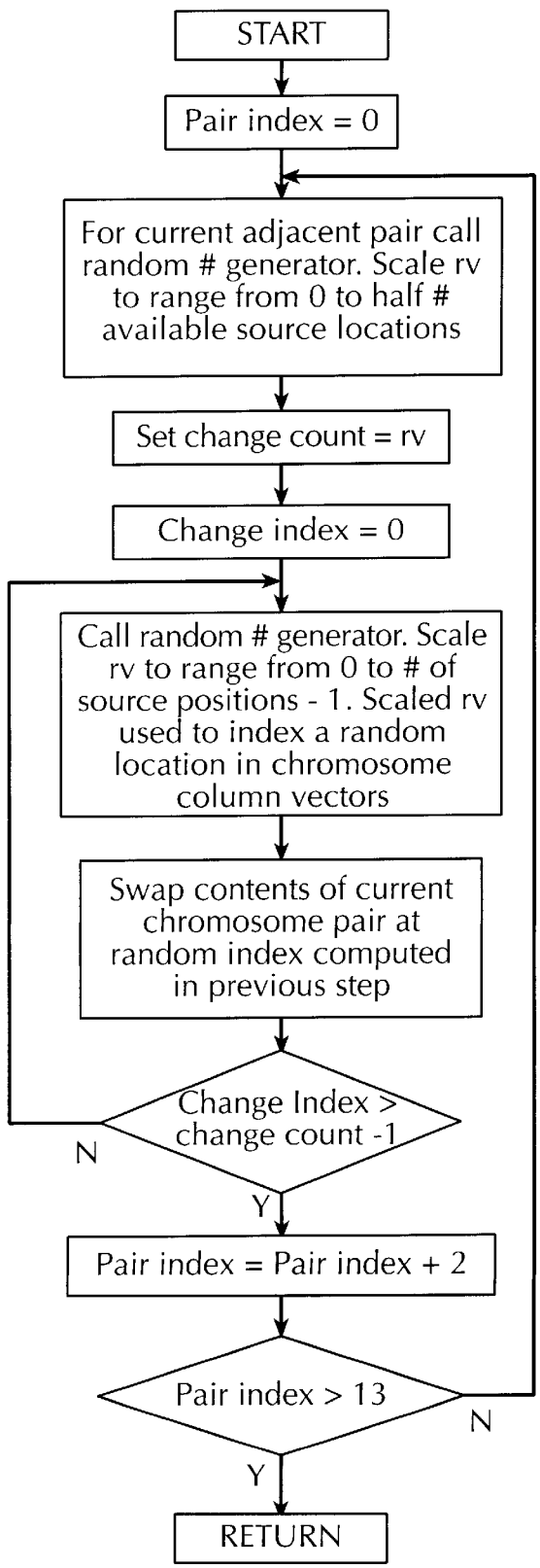
Figure 15F:
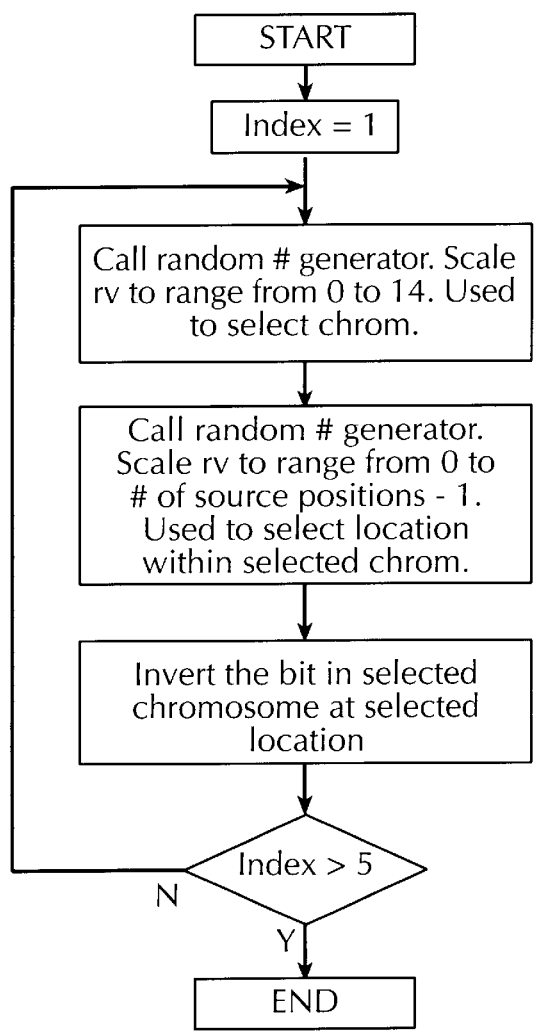
Figure 16A:
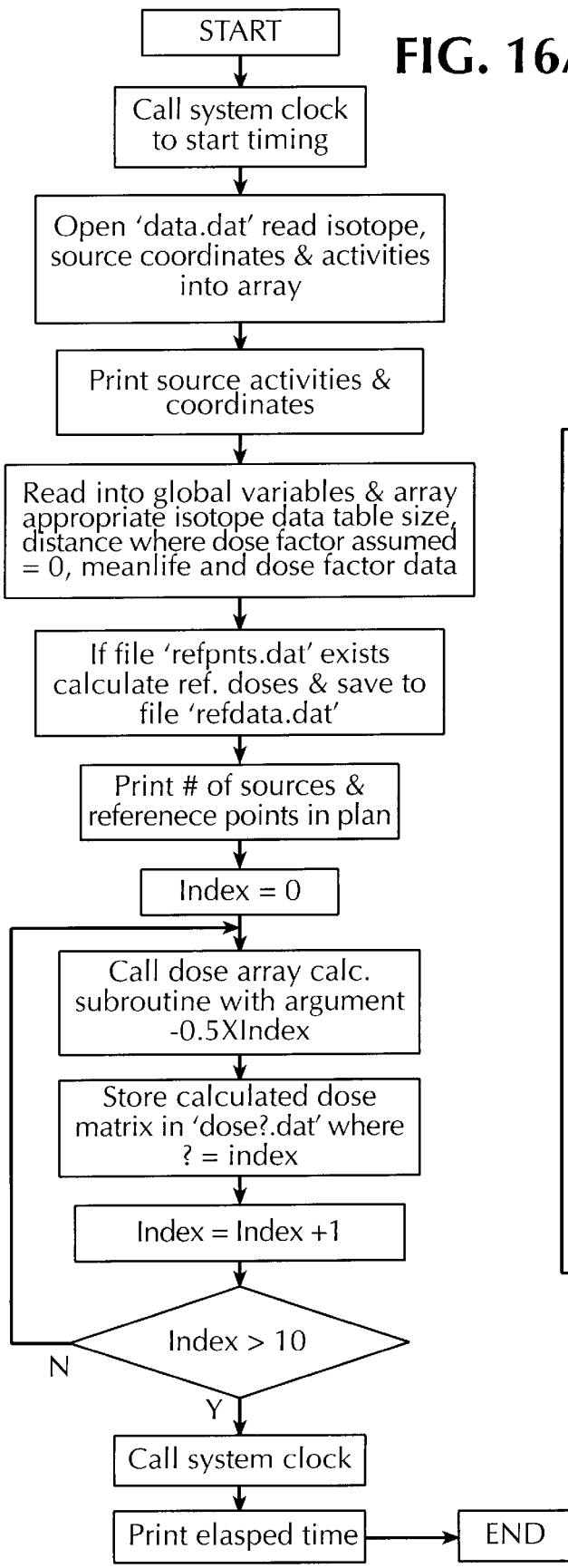
FIGS. 16A through 16D illustrate flow charts describing Module 6 of the computer program used by the system shown in FIG. 6.
Figure 16B:
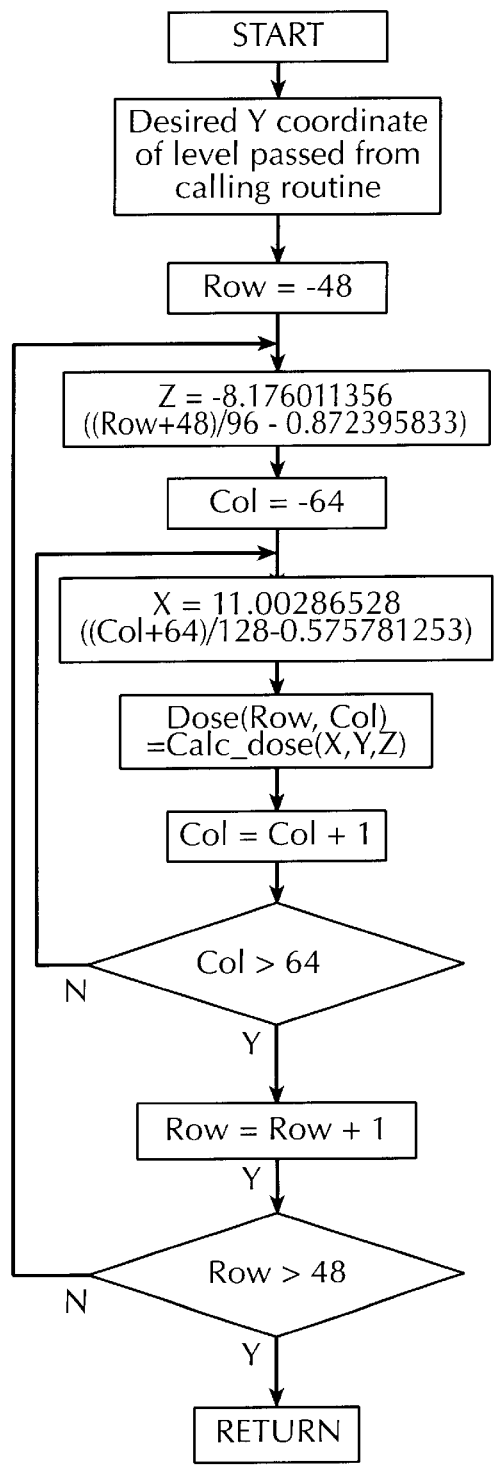
Figure 16C:
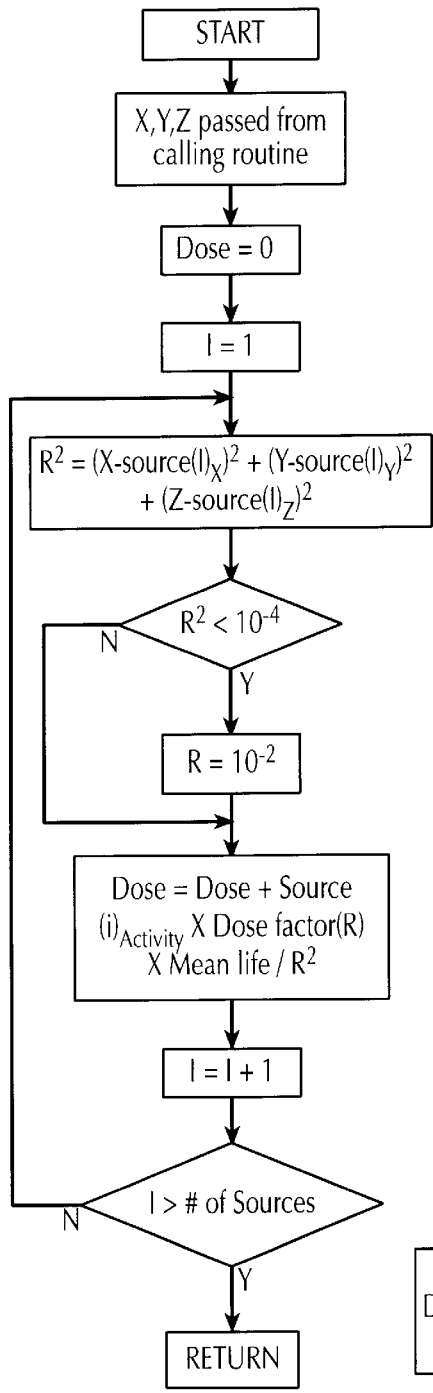
Figure 16D:
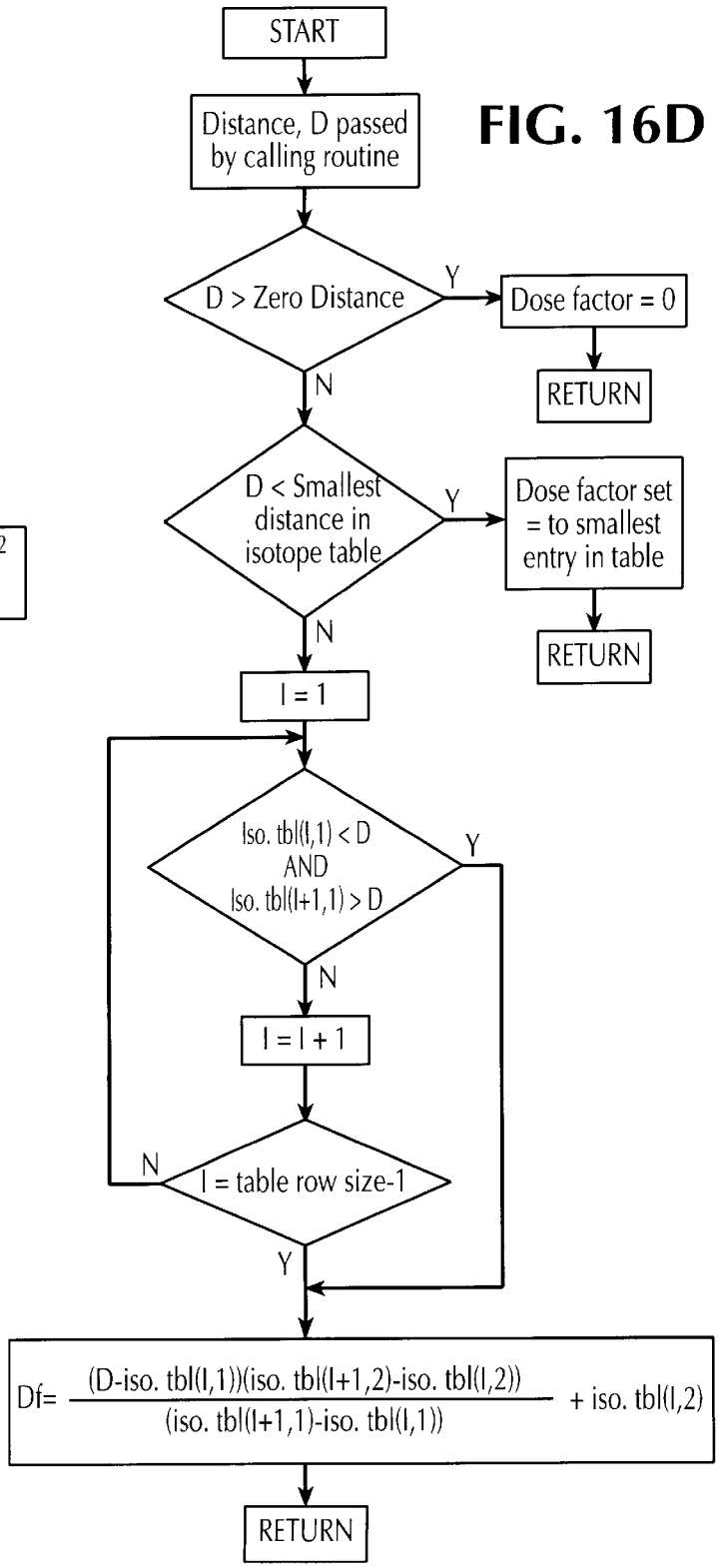

Specifically, referring to FIG. 15D, in step 41 the objective function calculates the individual dose at all contour points, uniformity points, rectal points and urethral points based on the source placement for each data stream in Table 1. Next, as shown in steps 43–47, the objective function calculates the three specific scores to evaluate the radiation dose applied to respectively to the rectum, urethra, and prostate. The rectal score 43 is defined as the number of points within the rectum whose dose is less than 78.26% of the prescribed dose. The urethral score 45 is defined as the number of points within the urethra which have a dose which is greater than the prescribed dose but less than 150% of the prescribed dose. The prostate score 47 is defined as the three times the number of points which surround the prostate which have a dose which is greater than or equal to the prescribed dose and less than 160% of the prescribed dose, plus the number of points within the prostate which have a dose which is greater than or equal to the prescribed dose and less than or equal to 160% of the prescribed dose.

After the three specific factors 43 through 47 are calculated, the objective function developed in accordance with the present invention then calculates a raw score 49. The raw score 49 is defined as thirty five times the rectal score 43 plus forty times the prostate score 45 plus the prostate score 47.

The objective function then calculates an overall score for each data stream based on the raw score 49. In particular, the objective function calculates an overall score by linearly scaling the raw score for each data stream in a range from 0 to 50. This is done by applying a formula in the form of Y=MX+B to the raw score 49 calculated for each data stream. In this formula, Y represents the linearly scaled overall score, X represents the raw score 49, and M and B represent constants. M and B are defined such that when X equals the lowest scoring member of the first generation Y equals 10, and when X equals the highest scoring member of the first generation, Y equals 50.

This formula is used to transform the raw scores 49 to overall scores for the first generation as well as all subsequently defined generations as will be described in detail below. Although, it should be noted that the constants M and B are calculated only once based on the values of the first generation and remain the same during the entire execution of Module 5. Therefore, in subsequent generations, should a data stream end up with an overall score of less than 10, it is set equal to 10.

In addition to calculating an overall score for each data stream, the second step of genetic algorithm calculates a cumulative overall score which will be discussed below. Table 1 shows an example of the overall scores as well as the cumulative overall scores calculated by the second step of the genetic algorithm.

The third step in the genetic algorithm developed in accordance with the present invention involves using scores of the objective function as criteria to select individuals to act as parents for the next generation. When selecting parents for the next generation, it is desirable to randomly select a data stream by favoring data streams with higher overall scores.

Reference will be made to Table 2 below to illustrate how the third step in the genetic algorithm developed in accordance with the present invention selects the desired number of patents.

TABLE 2

| POPULATION OF DATA STREAMS | | | | | | | | | | |
|---|---|---|---|---|---|---|---|---|---|---|
| RANDOM NUMBER | 120 | 91 | 99 | 49 | 51 | 132 | 2 | 129 | 138 | 121 |
| CUMULATIVE SCORE | 129 | 106 | 106 | 49 | 76 | 159 | 24 | 129 | 159 | 129 |
| 1 | 0 | 1 | 1 | 1 | 1 | 1 | 1 | 0 | 1 | 0 |
| 2 | 1 | 0 | 0 | 1 | 1 | 0 | 0 | 1 | 0 | 1 |
| . | 1 | 0 | 0 | 0 | 0 | 1 | 1 | 1 | 1 | 1 |
| . | 0 | 1 | 1 | 1 | 1 | 1 | 0 | 0 | 1 | 0 |
| . | 1 | 1 | 1 | 0 | 0 | 0 | 0 | 1 | 0 | 1 |
| . | 1 | 0 | 0 | 0 | 1 | 1 | 1 | 1 | 1 | 1 |
| . | 0 | 1 | 1 | 0 | 1 | 1 | 1 | 0 | 1 | 0 |
| . | 0 | 1 | 1 | 0 | 0 | 0 | 0 | 0 | 0 | 0 |
| . | 1 | 0 | 0 | 1 | 1 | 0 | 0 | 1 | 0 | 1 |
| N | 0 | 1 | 1 | 1 | 0 | 1 | 1 | 0 | 1 | 0 |
| OVERALL SCORE OF OBJECTIVE FUNCTION | 14 | 18 | 18 | 10 | 27 | 30 | 24 | 14 | 30 | 14 |

Figure 1:
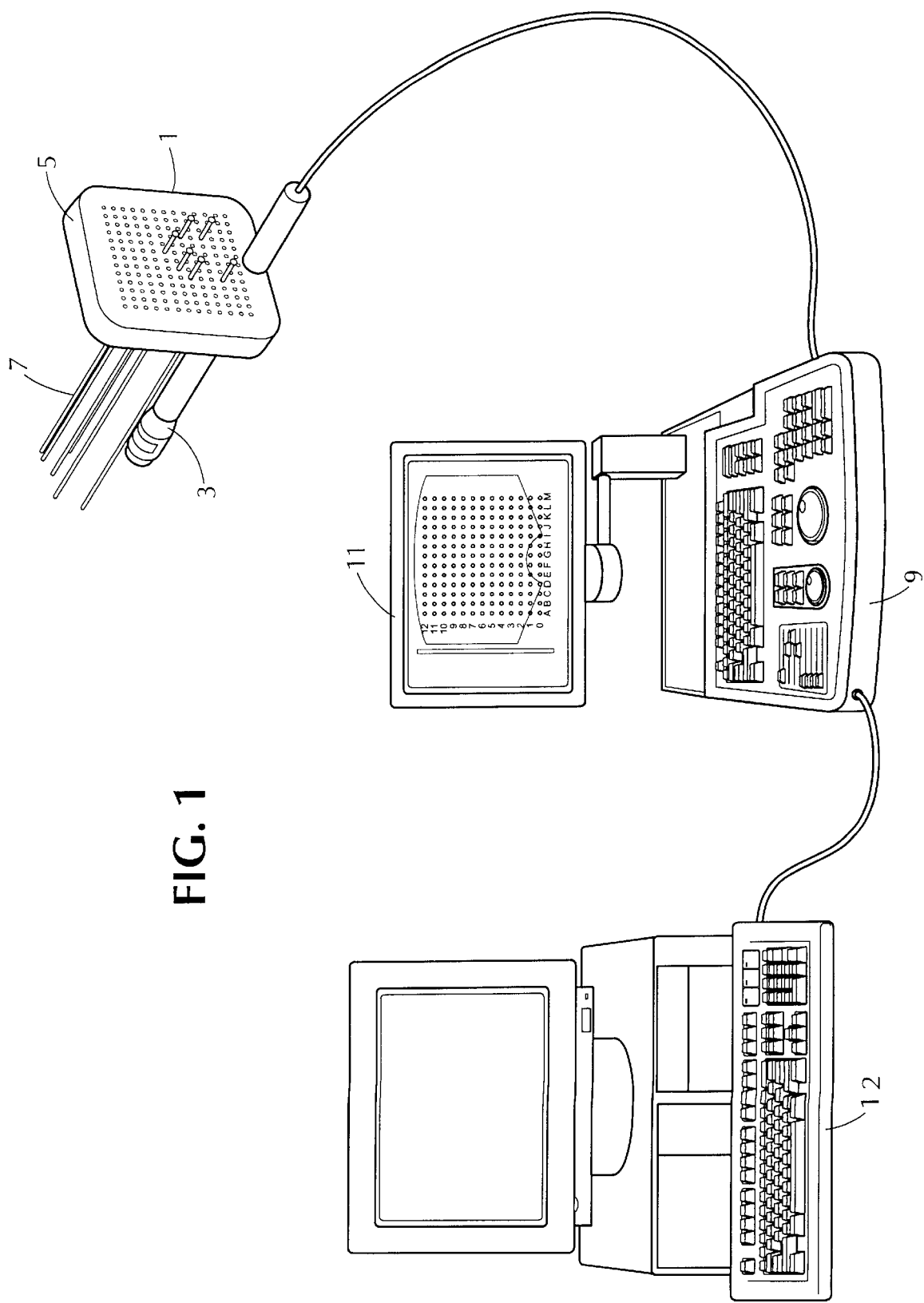
FIG. 1 illustrates a conventional system used to determine locations to place radioactive seeds at a cancerous site.
Figure 2:
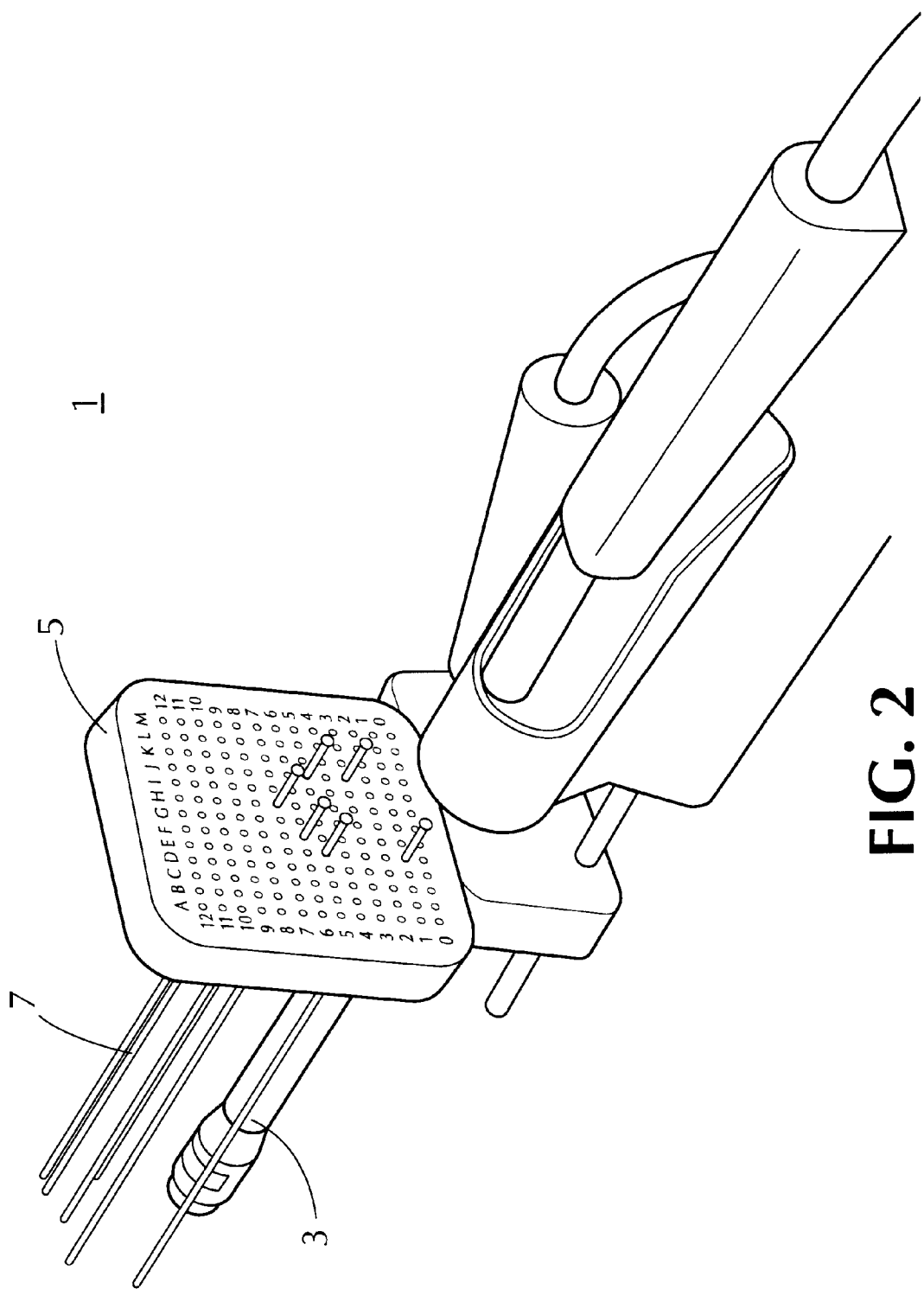
FIG. 2 illustrates a transducer used by the system shown in FIG. 1.
Figure 3:
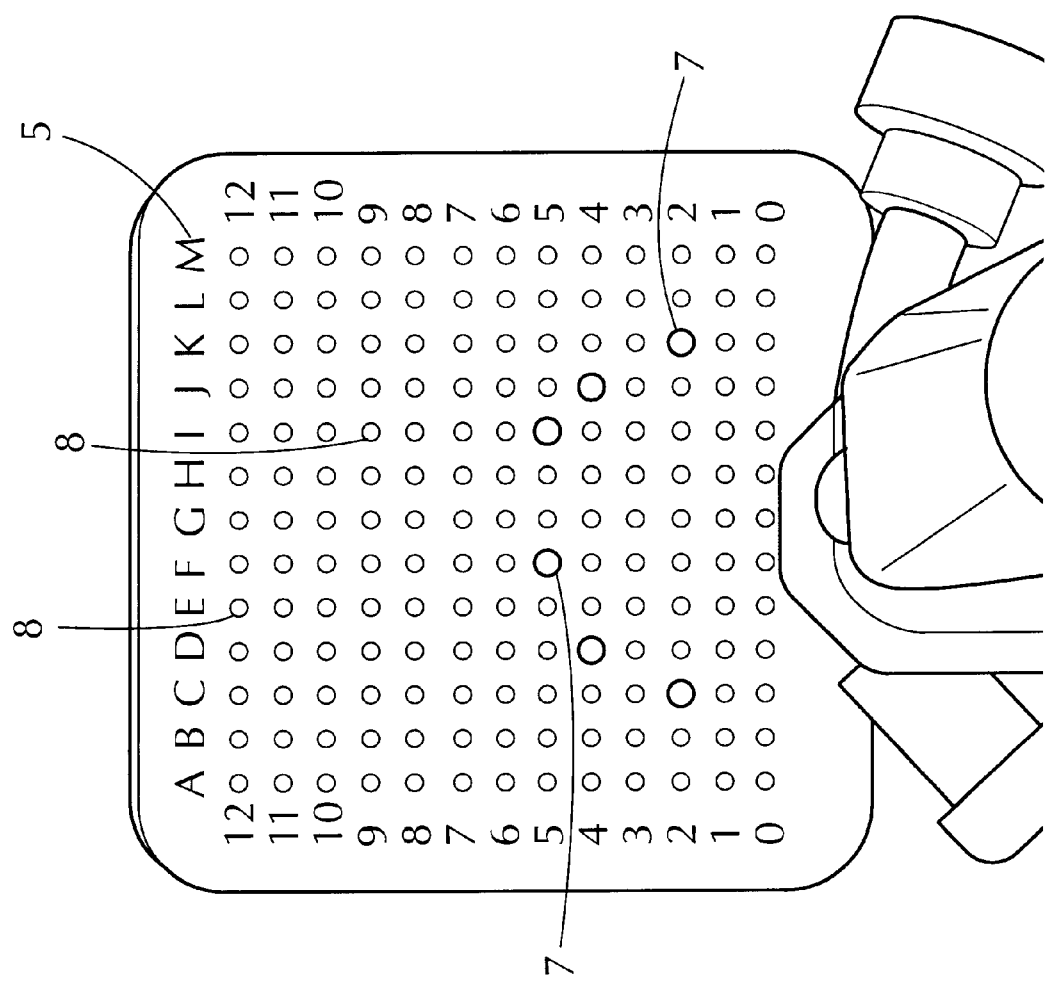
FIG. 3 illustrates a template used by the transducer shown in FIGS. 1 and 2.
Figure 4:
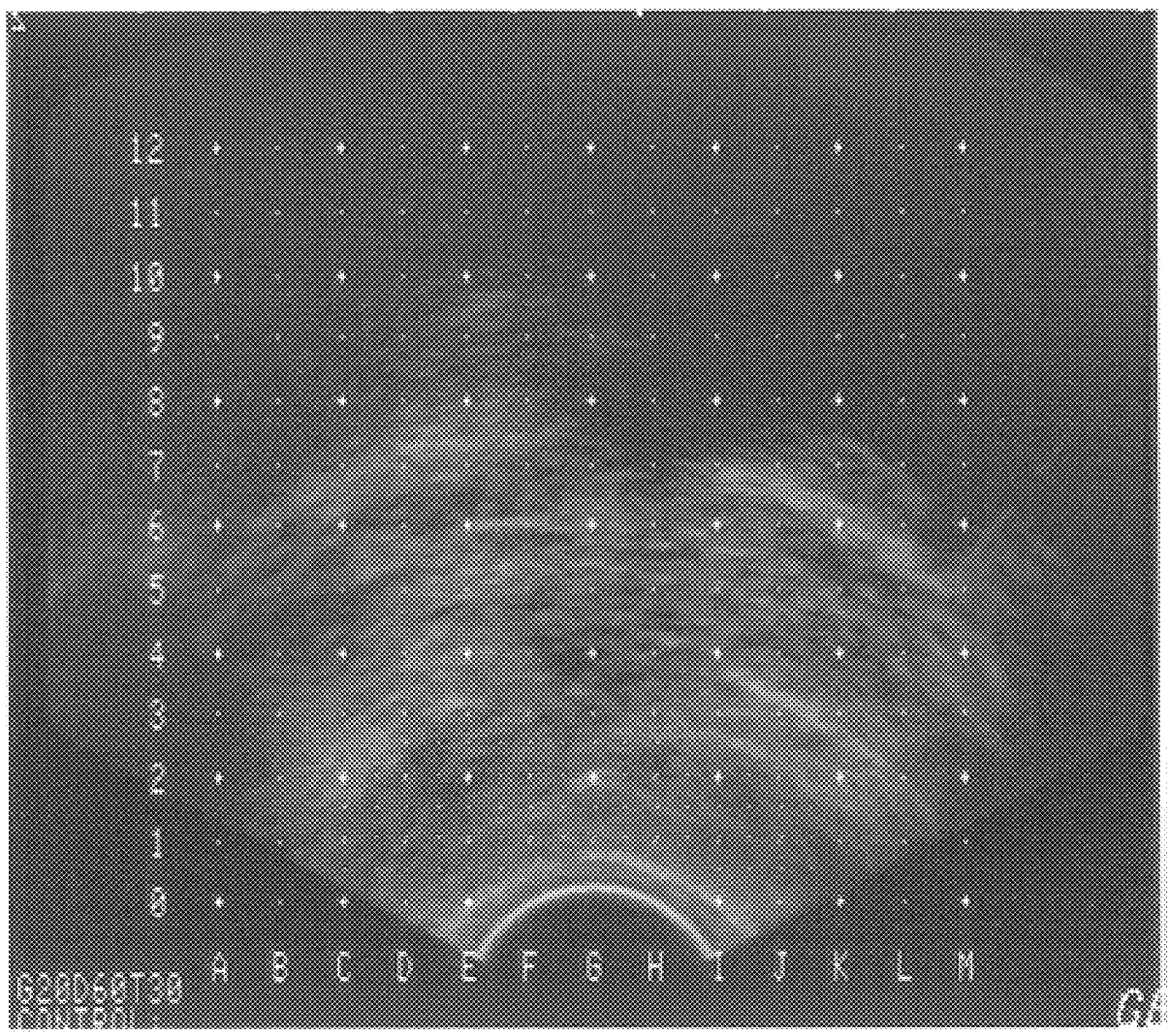
FIG. 4 illustrates an image displayed on a screen of the system shown in FIG. 1.
Figure 5:
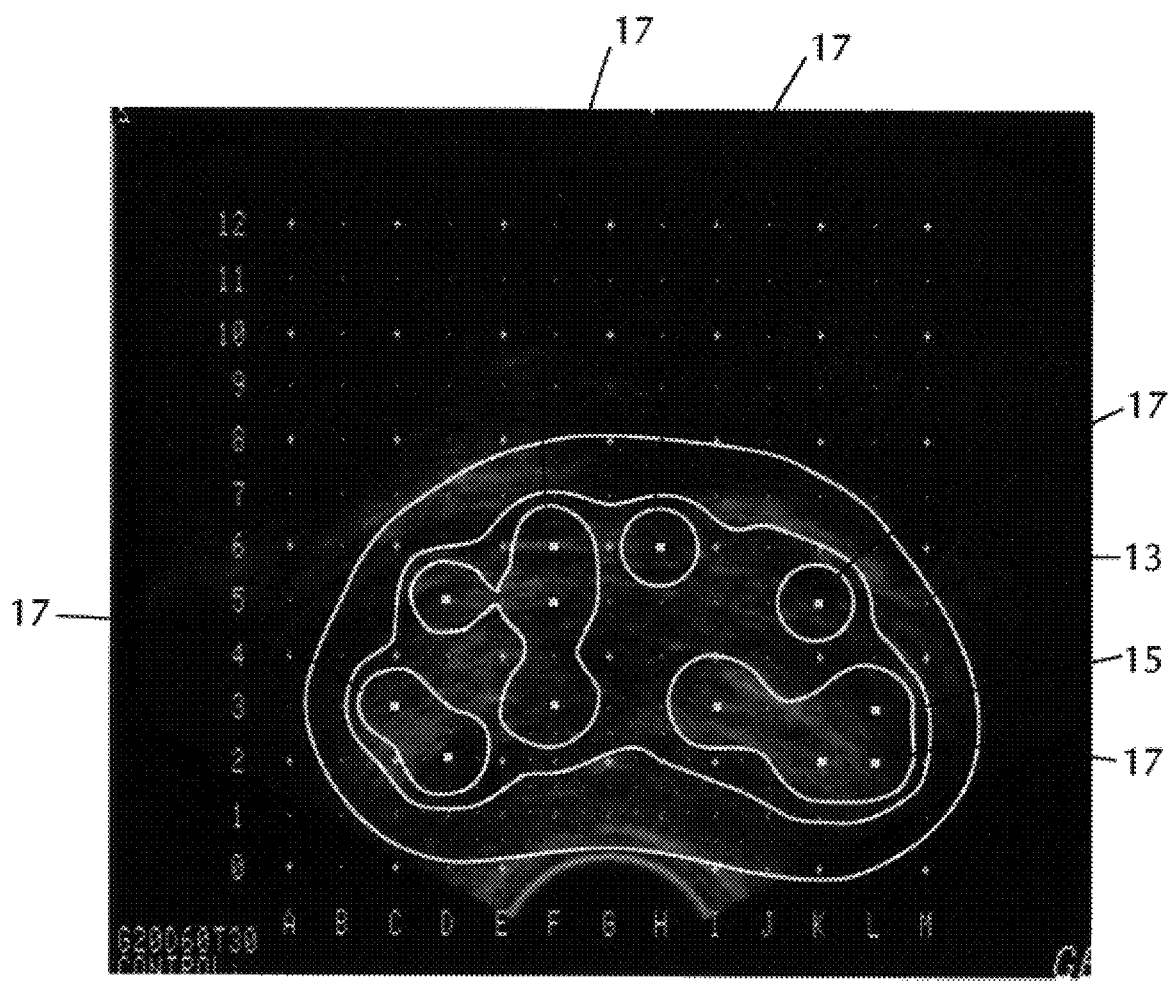
FIG. 5 illustrates another image displayed on the screen of the system shown in FIG. 1.

In the third step, a random number generator generates a series of ten random numbers from a uniformly distributed pool of numbers falling between 0 and 170 (i.e., the cumulative sum of all overall scores shown in FIG. 1). The ten generated random numbers are listed in the top row of Table 2. The random numbers are then matched with the data stream in Table 1 which contains the closest cumulative score which is not smaller than the generated random number.

For example, in Table 2 the fifth data stream from the left has a cumulative score of 76. The generated random number happened to be 51. Thus, the data stream with the closest cumulative score which is not smaller than 51 is selected which in this case happens to be the data stream with the overall score of 76.

Comparing Tables 1 and 2, one can see that higher scoring data streams were favored in the parent selection process. In particular, the average overall score of the data streams of Table 1 is 17, whereas, the average overall score of the data stream of Table 2 is 20.

After the parents are selected, the next step of the genetic algorithm developed in accordance with the present invention involves pairing off parents and mating the pairs by interchanging (i.e., "crossing over) some of the symbols. Crossover implemented by the genetic algorithm developed in accordance with the present invention randomly selects a varying number of data points in a pair and crosses over each of these points. The number of crossover points selected for a pair ranges between 0 and ½ of the possible number of source locations N.

This type of technique is illustrated in Table 3. In particular, each of the data points denoted by the letter c were crossed over from a 1 to a 0 or, alternatively, from a 0 to a 1.

TABLE 3

POPULATION OF DATA STREAMS

|   | PAIR 1 | | PAIR 2 | | PAIR 3 | | PAIR 4 | | PAIR 5 | |
|---|---|---|---|---|---|---|---|---|---|---|
| 1 | c1 | 0 | 1 | 1 | 1 | 1 | c0 | 1 | 1 | 0 |
| 2 | 1 | 0 | 0 | 1 | c0 | 1 | c1 | 0 | c1 | 0 |
| . | c0 | 1 | 0 | 0 | 0 | 1 | 1 | 1 | c1 | 1 |
| . | 0 | 1 | c1 | 1 | 1 | 1 | 0 | 0 | c0 | 1 |
| . | 1 | 1 | 1 | 0 | 0 | 0 | 0 | 1 | 0 | 1 |
| . | 1 | 0 | c0 | 0 | 1 | 1 | 1 | 1 | 1 | 1 |
| . | c1 | 0 | 1 | 0 | 1 | 1 | c0 | 1 | 1 | 0 |
| . | 0 | 1 | c0 | 1 | 0 | 0 | 0 | 0 | c0 | 0 |
| . | 1 | 0 | 0 | 1 | c0 | 1 | 0 | 1 | c1 | 0 |
| N | c1 | 0 | 1 | 1 | 0 | 1 | c0 | 1 | 1 | 0 |

The fifth step for the genetic algorithm involves performing mutations on the newly created data streams of Table 3. Mutation entails inverting bits at random locations in each of the data streams. A random number generator with an appropriate threshold is used to realize a mutation probability typically on the order of one percent. Bits of Table 4 below denoted by the letter m represent mutated bits of the data streams shown in Table 3. The number of mutations shown in Table 4 have been exaggerated for purposes of illustration.

TABLE 4

POPULATION OF DATA STREAMS

|   | PAIR 1 | | PAIR 2 | | PAIR 3 | | PAIR 4 | | PAIR 5 | |
|---|---|---|---|---|---|---|---|---|---|---|
| 1 | m0 | 0 | 1 | m0 | 1 | 1 | 0 | 1 | 1 | 0 |
| 2 | 1 | 0 | 0 | 1 | 0 | 1 | m0 | 0 | 1 | 0 |
| . | 0 | 1 | m1 | 0 | 0 | 1 | 1 | 1 | 1 | 1 |
| . | 0 | 1 | 1 | 1 | 1 | 0 | m1 | 0 | 1 | |
| . | 1 | 1 | 0 | 0 | 0 | 0 | 1 | 0 | m0 | |
| . | 1 | m1 | 0 | 0 | 1 | 1 | 1 | 1 | 1 | 1 |
| . | 1 | 0 | 1 | 0 | 1 | m0 | 0 | 1 | 1 | 0 |
| . | 0 | 1 | 0 | 1 | 0 | 0 | 0 | 0 | 0 | 0 |
| . | 1 | 0 | 0 | 1 | 0 | 1 | 0 | 1 | m0 | 0 |
| N | 1 | 0 | 1 | 1 | m1 | 1 | 0 | 1 | 1 | 0 |

The sixth step in the genetic algorithm developed in accordance with present invention involves replacing one data stream in Table 4 with the highest scoring data stream of the previous generation of data streams shown in Table 1. This ensures that the highest scoring data stream from the previous generation survives and becomes part of the next generation.

By way of example, in the sixth step, the ninth column of Table 1 (i.e, the data stream of the previous generation having the highest score) replaces the ninth column of Table 4 to define the next generation of data streams. Table 5 below shows this next generation of data streams produced by the step six of the genetic algorithm developed in accordance with the present invention.

TABLE 5

POPULATION OF DATA STREAMS

|   | PAIR 1 | | PAIR 2 | | PAIR 3 | | PAIR 4 | | PAIR 5 | |
|---|---|---|---|---|---|---|---|---|---|---|
| 1 | 0 | 0 | 1 | 0 | 1 | 1 | 0 | 1 | *1 | 0 |
| 2 | 1 | 0 | 0 | 1 | 0 | 1 | 0 | 0 | *0 | 0 |
| . | 0 | 1 | 1 | 0 | 0 | 1 | 1 | 1 | *1 | 1 |
| . | 0 | 1 | 1 | 1 | 1 | 1 | 0 | 1 | *1 | 1 |
| . | 1 | 1 | 0 | 0 | 0 | 0 | 1 | *0 | 0 | |
| . | 1 | 1 | 0 | 0 | 1 | 1 | 1 | 1 | *1 | 1 |
| . | 1 | 0 | 1 | 0 | 1 | 0 | 0 | 1 | *1 | 0 |
| . | 0 | 1 | 0 | 1 | 0 | 0 | 0 | 0 | *0 | 0 |
| . | 1 | 0 | 0 | 1 | 0 | 1 | 0 | 1 | *0 | 0 |
| N | 1 | 0 | 1 | 1 | 1 | 1 | 0 | 1 | *1 | 0 |

*Denotes column replaced with highest scoring data stream from previous generation The seventh step in the genetic algorithm developed in accordance with the present invention involves evaluating each member of the new generation of data streams shown in Table 5 by applying the objective function discussed above. The genetic algorithm then, in step eight, repeats steps three through seven until the desired number of generations are modeled. Usually 2000 generations are modeled by the genetic algorithm developed in accordance with present invention.

The last step performed by the genetic algorithm used by Module 5 involves selecting the highest scoring stream. Once this step is performed, a treatment plan for the patient has been defined.

MODULE 6

Module 6 of the optimization computer program is known as the dosimetry module and is used to evaluate the treatment plan defined by Module 5. A flow chart describing this module is shown in FIGS. 16A through 16D, whereas, a listing of the source code is provided in Appendix 6 of the microfiche submitted herewith.

Module 6 calculates the radiation levels produced at uniformly spaced locations in a rectangular area corresponding to the ultrasound image as result of the number, location, and strength of seeds identified by Module 5. Seven dosimetry matrices corresponding to the locations of the seven levels of ultrasound images are calculated and stored to the hard drive of the optimization unit 21. These files will be used by Modules 7–9 as described below. In addition, of the file "refpnts.dat" exists the doses at the reference coordinates are calculated and stored in a file called "refdata.dat." This feature is used for calculating urethral and rectal point doses.

The three dimensional coordinate system discussed above in Module 2 is defined such that the coordinate system's origin coincides with needle grid location G0 on the patient's most superior ultrasound image. In this coordinate system, the positive X direction is toward the patient's left, and the negative X direction is toward the patient's right. Also, the positive Y direction is in the superior direction and the negative Y direction is in the inferior direction. In regard to this axis of the coordinate system, the Y origin is defined at the patient's most superior level (i.e., Level 0). As such, all Y coordinates are either 0 (i.e., positioned at the most superior level) or negative. Also, since each of the images are positioned at 5 mm apart, each of the Y coordinate values are integral multiples of 5 mm. For example, the Y coordinate corresponding to Level 6 would be −30 mm or −3.0 cm. Lastly, in the coordinate system, the positive Z direction is toward the patient's anterior surface and the negative Z direction is toward the patient's posterior surface.

MODULE 7

Figure 17:
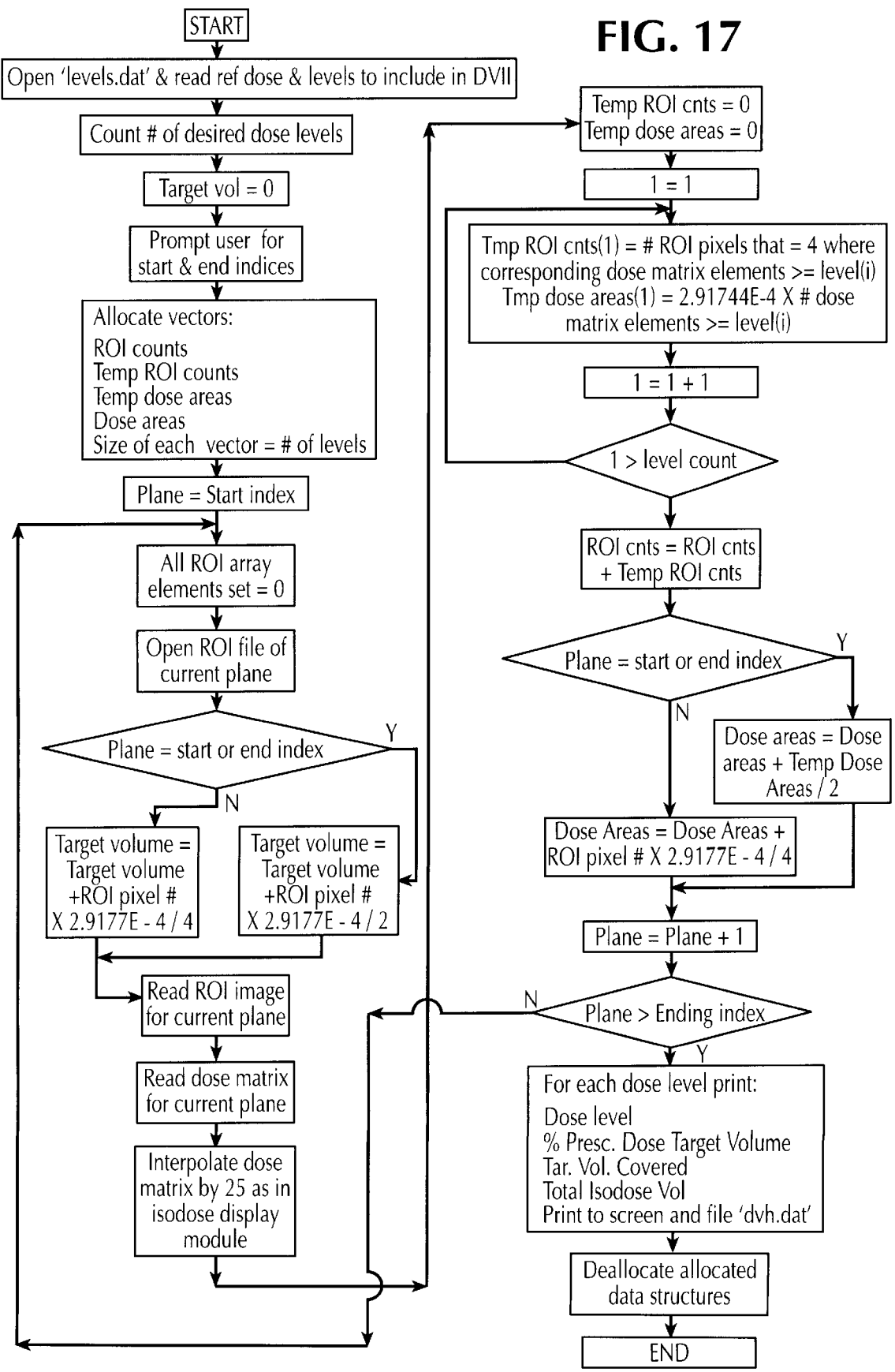
FIG. 17 illustrates a flow chart describing Module 7 of the computer program used by the system shown in FIG. 6.

Module 7 of the optimization computer program is known as the dose-volume-histogram (DVH) module. A flow chart describing this module is shown in FIG. 17, whereas, a listing of the source code is provided in Appendix 7 of the microfiche submitted herewith.

Module 7 computes the prostrate volume, the prostrate volume covered by various isodose levels, the % of the prostrate covered by the various isodose levels, as well as the other factors, such as the total volume in the prostrate region covered by the various isodose levels.

Table 6 below summarizes these measurements calculated by Module 7 is shown below assuming a prescribed isodose of 16000 cGy.

TABLE 6

| Various Isodose Levels of cGy | % Of Prescription Dose | Prostate Volume (cc) | Prostate Volume Covered By Various Isodose Levels | % of Prostate Volume Covered By Various Isodose Levels | Total Isodose Volume in Prostate Region |
|---|---|---|---|---|---|
| 8000.0 | 50.0 | 22.9 | 22.9 | 100.0 | 51.3 |
| 16000.0 | 100.0 | 22.9 | 22.2 | 96.8 | 26.6 |
| 24000.0 | 150.0 | 22.9 | 10.9 | 47.7 | 11.5 |

MODULE 8

Figure 18A:
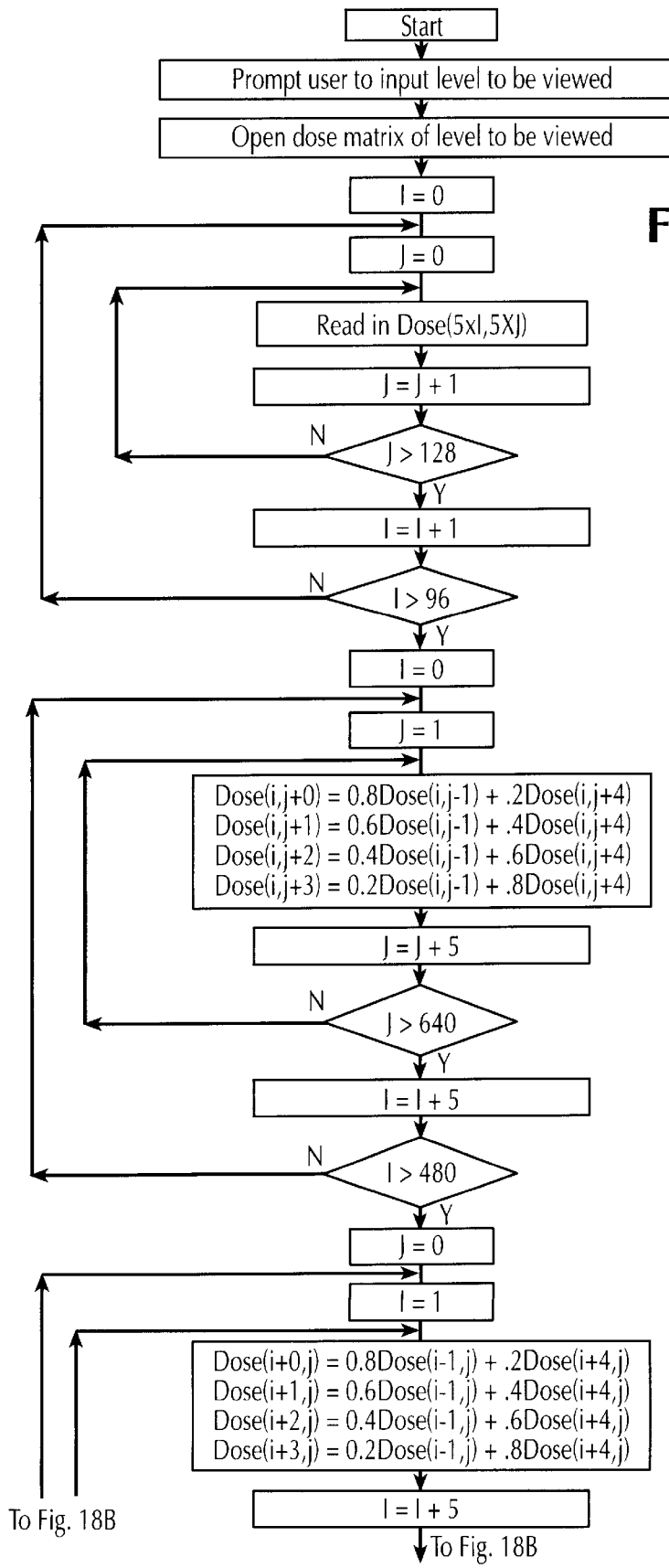
FIGS. 18A through 18C illustrates a flow chart describing Module 8 of the computer program used by the system shown in FIG. 6.
Figure 18B:
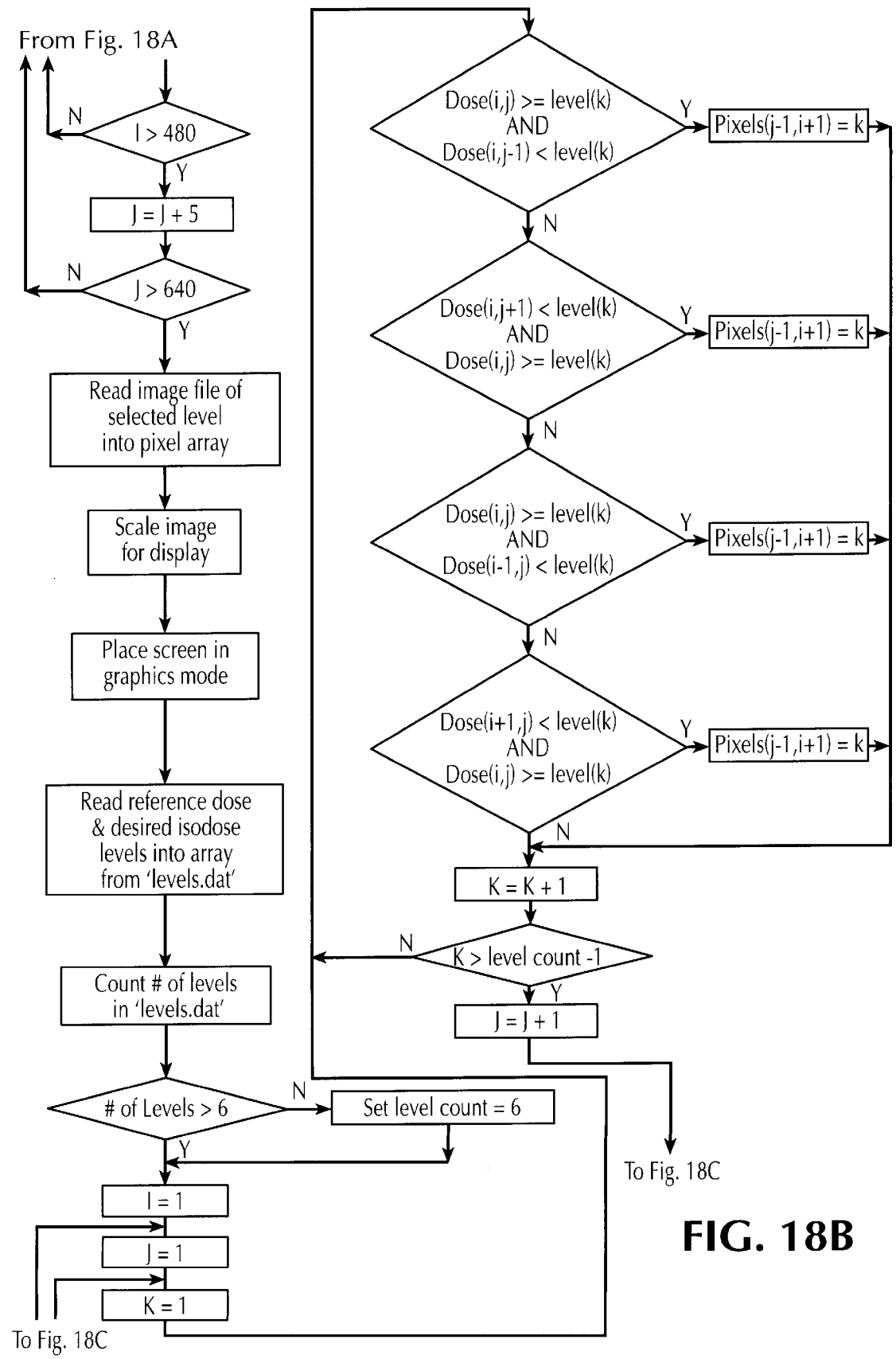
Figure 18C:
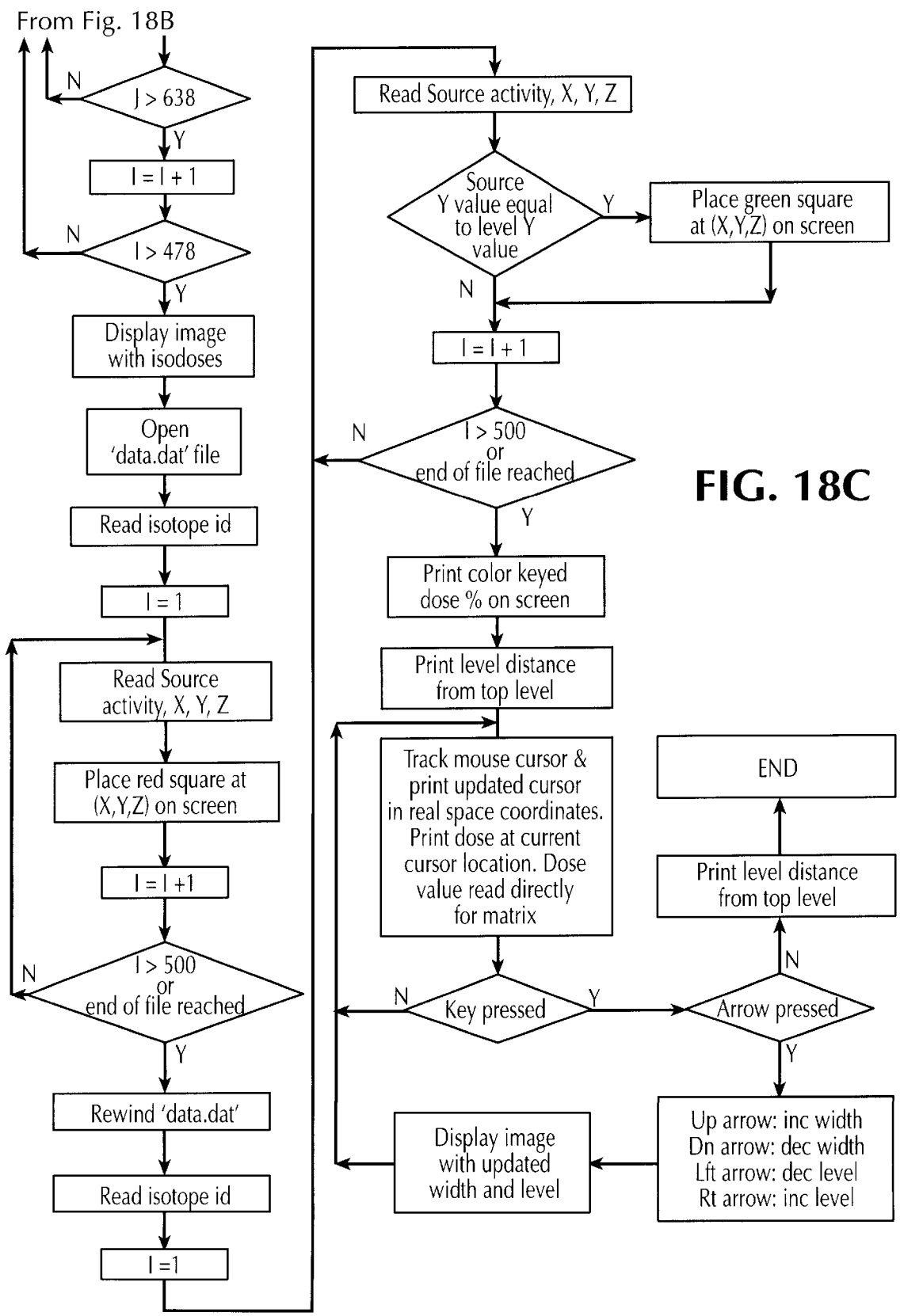

Module 8 of the optimization computer program is known as the isodose display module. A flow chart describing Module 8 is shown in FIGS. 18A through 18C, whereas, a listing of the source code is provided in Appendix 8 of the microfiche submitted herewith.

Figure 19:
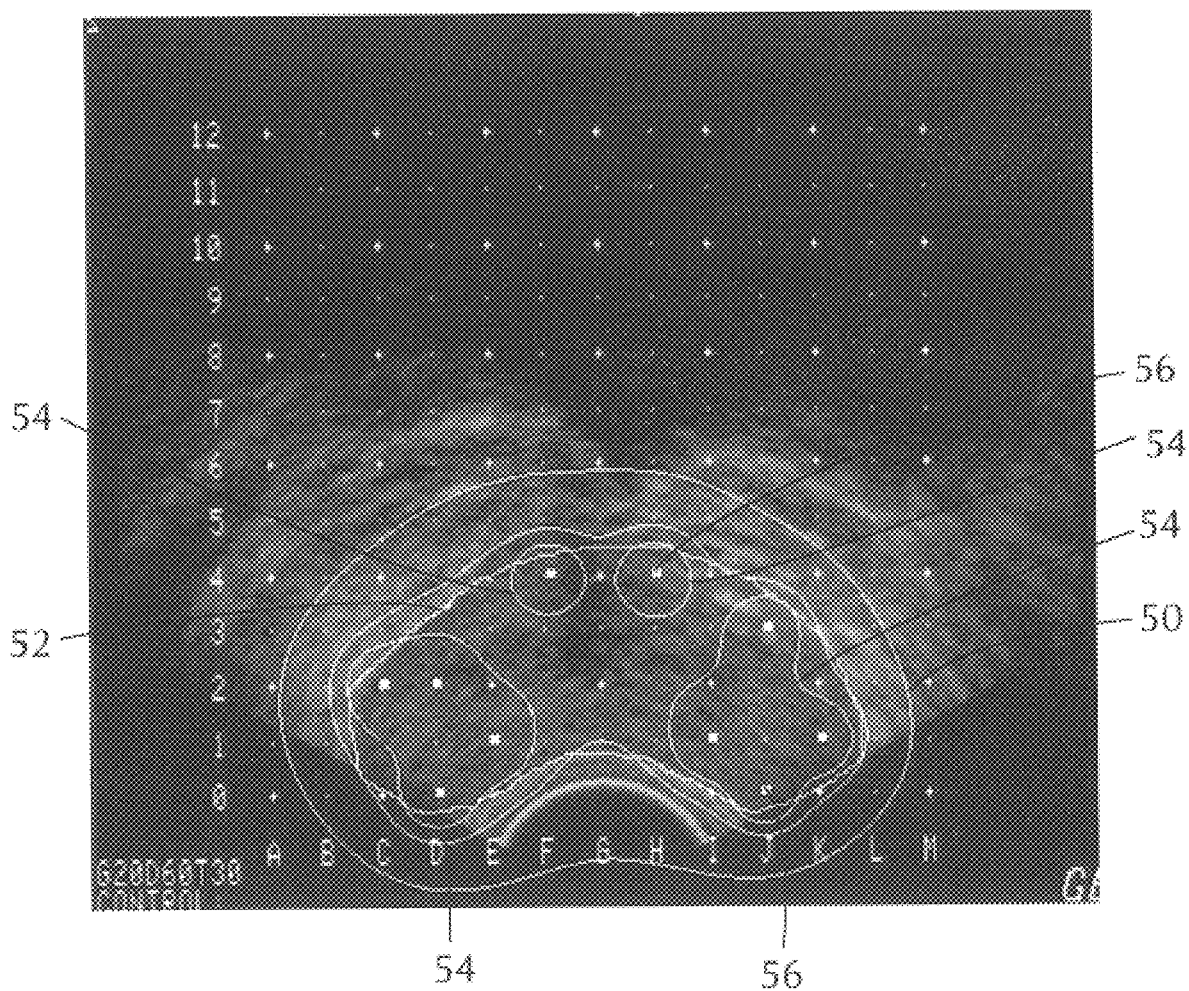
FIG. 19 illustrates an image displayed on the screen of the system shown in FIG. 6.

Module 8 displays the isodose contours by using the dosimetry values calculated by Module 6 on each of the ultrasound images captured for each level. In particular, referring to FIG. 19, the outer contour line 50 encloses an area of the prostate which receives at least 50% of the prescribed radiation dose. Although not shown in the drawing, this line would typically be coded with a unique color. The middle contour line 52 encloses an area of the prostate which would receive at least 100% of the prescribed radiation dose, whereas, the multiple contour lines 54 enclose those areas of the prostate which receive at least 150% of the prescribed radiation dose. Contour lines 52 and 54 are similarly coded with a unique color.

The needle and source coordinates 56 are additionally superimposed on the screen. Also, the mouse cursor can be moved anywhere on the screen and the dose at the cursor location is displayed to the operator. Windowing and leveling functions are additionally available from the module via the arrow keys on the keyboard.

MODULE 9

Figure 20:
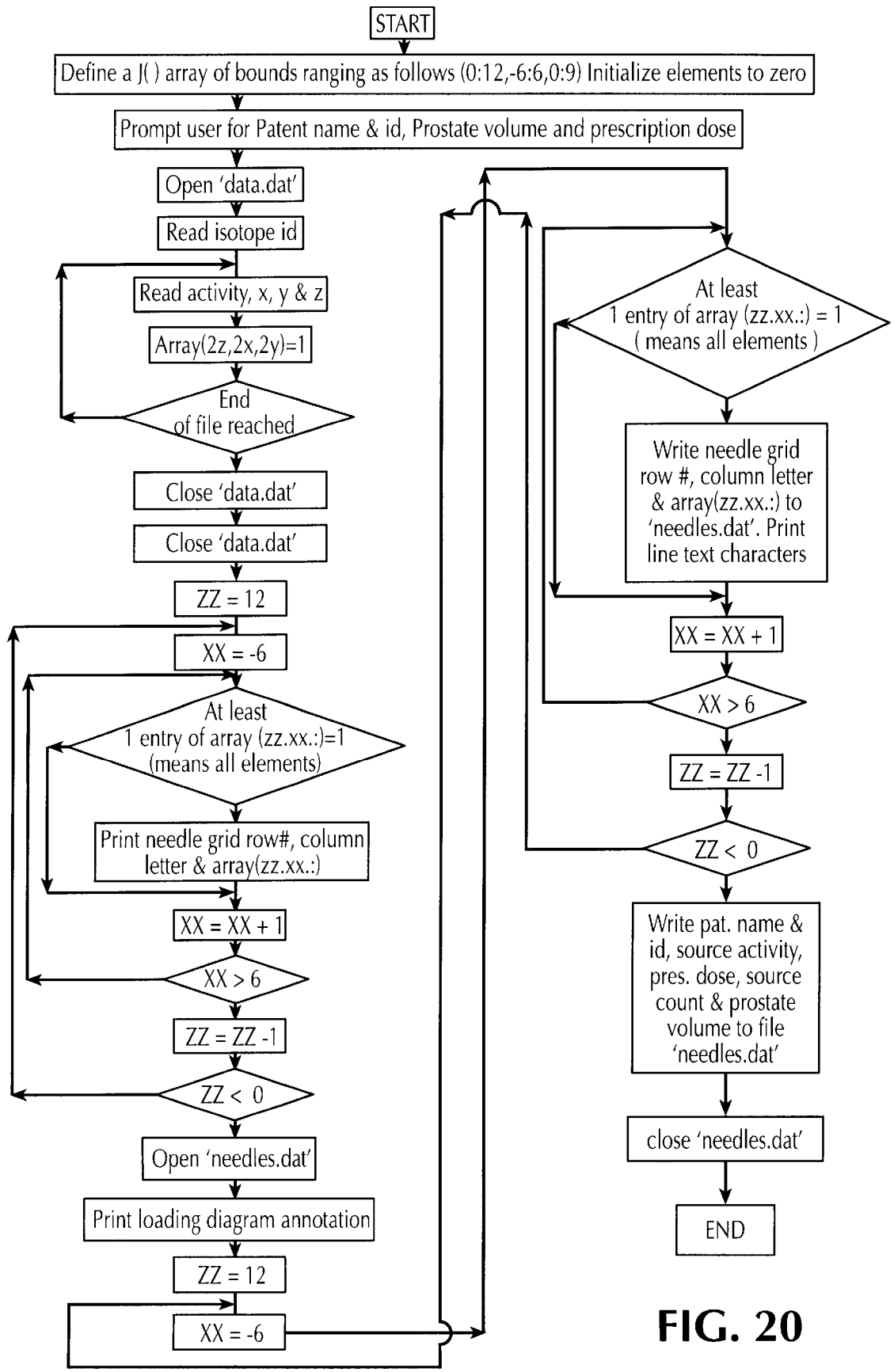
FIG. 20 illustrates a flow chart describing Module 9 of the computer program used by the system shown in FIG. 6; and, FIG. 21 illustrates a sample needle diagram produced by the system shown in FIG. 6.

Module 9 of the optimization computer program is known as the loading generator diagram module. A flow chart describing Module 9 is shown in FIG. 20, whereas, a listing of the source code is provided in Appendix 9 of the microfiche submitted herewith.

Module 9 produces a needle loading diagram of the treatment plan generated by the aforementioned modules. FIG. 21 shows a sample needle loading diagram. Referring to the diagram, the left hand column represents the needle loading diagram for the most superior ultrasound image, which is L0, and the right hand column represents the most inferior image which is L6. A "1" on the diagram represents the placement of a radioactive source, whereas, a "0" represents an empty needle site.

Various other types of information are provided on the chart as well. For example the patient's name, patient's identification number, prostate volume, number of radioactive sources, and the type of isotope can be included on the diagram. A printout of the loading diagram is used in the operating room to aid in the needle and source placement during the implant procedure.

Each of the nine modules described above operate in combination to constitute that optimization computer program which, in accordance with the present invention, determines the optimal location for placing radioactive seeds at a cancerous site. The invention is not, however, to be considered limited in scope by the preferred embodiments described in the specification. Additional advantages and modifications, which will readily occur to those skilled in the art from consideration of the specification and practice of the invention, are intended to be within the scope and spirit of the following claims.

I claim:

1. A method for determining optimal locations for placing radioactive seeds at a cancerous prostate, said method comprising the steps of:

(a) obtaining a plurality of cross-sectional images of the prostate;

(b) tracing a contour of an area on each cross-sectional image of the prostate obtained from step (a);

(c) transferring the contour and area of each cross-sectional image of the prostate defined in step (b) to a three-dimensional coordinate system;

(d) defining a population of locations within each area of each cross-sectional image of the prostate where radioactive seeds can be placed;

(e) defining a location of the urethra within each area of each cross-sectional image of the prostate;

(f) using a genetic algorithm to determine an optimal number of locations within the prostate to place the radioactive seeds;

(g) determining radiation levels within the prostate based on the optimal number of locations defined by step (f);

(h) identifying portions of the prostate which receive various levels of a prescribed radiation dose;

(i) displaying contours on each cross-sectional image of the prostate which show the portions defined in step (h); and (j) producing a treatment plan showing the optimal number of locations within the prostate where the radioactive seeds are to be placed.

2. The method for determining optimal locations for placing radioactive seeds at a cancerous prostate according to claim 1, wherein said genetic algorithm used by step (f) further includes the steps of:

(f1) selecting symbol streams to model the optimal number of locations within the prostate where the radioactive seeds can be placed;

(f2) applying an objective function to calculate an overall score for each selected symbol stream obtained from step (f1);

(f3) selecting symbol streams evaluated in step (f2) to act as parents for a subsequent generation of symbol streams based on the overall scores calculated by the objective function;

(f4) mating pairs of symbol streams defined by step (f3) to be parents by interchanging various symbols;

(f5) performing mutations on the symbol streams defined by step (f4);

(f6) replacing a symbol stream from step (f5) with the highest scoring symbol stream from step (f2) to define the subsequent generation of symbol streams;

(f7) applying the objective function to calculate an overall score for each member of the subsequent generation of symbol streams obtained from step (f6);

(f8) repeating steps (f3) through (f7) until a desired generation count is reached; and (f9) selecting the symbol stream with the highest overall score.

3. The method for determining optimal locations for placing radioactive seeds at a cancerous prostate according to claim 2, wherein the overall score calculated by the objective function is a based on a weighted sum of a rectal score, a urethral score and a prostate score.

4. The method for determining optimal locations for placing radioactive seeds at a cancerous prostate according to claim 3, wherein: (i) the rectal score is defined as the number of points within the rectum whose dose is less than 78.26% of the prescribed dose; (ii) the urethral score is defined as the number of points within the urethra which have a dose which is greater than the prescribed dose but less than 150% of the prescribed dose; and, (iii) the prostate score is defined as the three times the number of points which surround the prostate which have a dose which is greater than or equal to the prescribed dose and less than 160% of the prescribed dose, plus the number of points within the prostate which have a dose which is greater than or equal to the prescribed dose and less than or equal to 160% of the prescribed dose.

5. An apparatus for determining optimal locations for placing radioactive seeds at a cancerous prostate, said apparatus comprising:

(a) means for obtaining a plurality of cross-sectional images of the prostate;

(b) means for tracing a contour of an area on each cross-sectional image of the prostate obtained from means (a);

(c) means for transferring the contour and area of each cross-sectional image of the prostate defined by means (b) to a three-dimensional coordinate system;

(d) means for defining a population of locations within each area of each cross-sectional image of the prostate where radioactive seeds can be placed;

(e) means for defining a location of the urethra within each area of each cross-sectional image of the prostate;

(f) means for using a genetic algorithm to determine an optimal number of locations within the prostate to place the radioactive seeds;

(g) means for determining radiation levels within the prostate based on the optimal number of locations defined by means (f);

(h) means for identifying portions of the prostate which receive various levels of a prescribed radiation dose;

(i) means for displaying contours on each cross-sectional image of the prostate which show the portions defined in step (h); and (j) means for producing a treatment plan showing the optimal number of locations within the prostate where the radioactive seeds are to be placed.

6. The apparatus for determining optimal locations for placing radioactive seeds at a cancerous prostate according to claim 5, wherein said means for using a genetic algorithm further includes:

(f1) means for selecting symbol streams to model the optimal number of locations within the prostate where the radioactive seeds can be placed;

(f2) means for applying an objective function to calculate an overall score for each selected symbol stream obtained by means (f1);

(f3) means for selecting symbol streams evaluated by means (f2) to act as parents for a subsequent generation of symbol streams based on the overall scores calculated by the objective function;

(f4) means for mating pairs of symbol streams defined by means (f3) to be parents by interchanging various symbols;

(f5) means for performing mutations on the symbol streams defined by means (f4);

(f6) means for replacing a symbol stream defined by means (f5) with the highest scoring symbol stream defined by means (f2) to define the subsequent generation of symbol streams;

(f7) means for applying the objective function to calculate an overall score for each member of the subsequent generation of symbol streams obtained by means (f6);

(f8) means for reactivating means (f3) through (f7) until a desired generation count is reached; and (f9) means for selecting the symbol stream with the highest overall score.

7. The apparatus for determining optimal locations for placing radioactive seeds at a cancerous prostate according to claim 6, wherein the overall score calculated by the objective function is a based on a weighted sum of a rectal score, a urethral score and a prostate score.

8. The apparatus for determining optimal locations for placing radioactive seeds at a cancerous prostate according to claim 7, wherein: (i) the rectal score is defined as the number of points within the rectum whose dose is less than 78.26% of the prescribed dose; (ii) the urethral score is defined as the number of points within the urethra which have a dose which is greater than the prescribed dose but less than 150% of the prescribed dose; and, (iii) the prostate score is defined as the three times the number of points which surround the prostate which have a dose which is greater than or equal to the prescribed dose and less than 160% of the prescribed dose, plus the number of points within the prostate which have a dose which is greater than or equal to the prescribed dose and less than or equal to 160% of the prescribed dose.

9. A method for determining optimal locations for placing radioactive seeds at a cancerous site, said method comprising the steps of:

(a) obtaining a plurality of cross-sectional images of the cancerous site;

(b) tracing a contour of an area on each cross-sectional image of the cancerous site obtained from step (a);

(c) transferring the contour and area of each cross-sectional image of the cancerous site defined by step (b) to a three-dimensional coordinate system;

(d) defining a population of locations within each area of each cross-sectional image of the cancerous site where radioactive seeds can be placed; and, (e) using a genetic algorithm to determine an optimal number of locations within the cancerous site to place the radioactive seeds.

10. The method for determining optimal locations for placing radioactive seeds at a cancerous site according to claim 9, wherein step (e) which uses a genetic algorithm further includes the steps of:

(f1) selecting symbol streams to model the optimal number of locations within the cancerous site where the radioactive seeds can be placed;

(f2) applying an objective function to calculate an overall score for each selected symbol stream obtained by step (f1);

(f3) selecting symbol streams calculated by step (f2) to act as parents for a subsequent generation of symbol streams based on the overall scores calculated by the objective function;

(f4) mating pairs of symbol streams defined by step (f3) to be parents by interchanging various symbols;

(f5) performing mutations on the symbol streams defined by step (f4);

(f6) replacing a symbol stream from step f(5) with the highest scoring symbol stream from step (f2) to define the subsequent generation of symbol streams;

(f7) applying the objective function to calculate an overall score for each member of the subsequent generation of symbol streams obtained by step (f6);

(f8) repeating steps (f3) through (f7) until a desired generation count is reached; and (f9) selecting the symbol stream with the highest overall score.

11. An apparatus for determining optimal locations for placing radioactive seeds at a cancerous site, said apparatus comprising:

(a) means for obtaining a plurality of cross-sectional images of the cancerous site;

(b) means for tracing a contour of an area on each cross-sectional image of the cancerous site obtained from means (a);

(c) means for transferring the contour and area of each cross-sectional image of the cancerous site defined by means (b) to a three-dimensional coordinate system;

(d) means for defining a population of locations within each area of each cross-sectional image of the cancerous site where radioactive seeds can be placed; and, (e) means for using a genetic algorithm to determine an optimal number of locations within the cancerous site to place the radioactive seeds.

12. The apparatus for determining optimal locations for placing radioactive seeds at a cancerous site according to claim 11, wherein said means for using a genetic algorithm further includes:

(f1) means for selecting symbol streams to model the optimal number of locations within the cancerous site where the radioactive seeds can be placed;

(f2) means for applying an objective function to calculate an overall score for each selected symbol stream obtained by means (f1);

(f3) means for selecting symbol streams evaluated by means (f2) to act as parents for a subsequent generation of symbol streams based on the overall scores calculated by the objective function;

(f4) means for mating pairs of symbol streams defined by means (f3) to be parents by interchanging various symbols;

(f5) means for performing mutations on the symbol streams defined by means (f4);

(f6) means for replacing a symbol stream defined by means (f5) with the highest scoring symbol stream defined by means (f2) to define the subsequent generation of symbol streams;

(f7) means for applying the objective function to calculate an overall score for each member of the subsequent generation of symbol streams obtained by means (f6);

(f8) means for reactivating means (f3) through (f7) until a desired generation count is reached; and (f9) means for selecting the symbol stream with the highest overall score.

* * * * *